US012657713B2

(12) United States Patent
Matthews et al.

(10) Patent No.: US 12,657,713 B2
(45) Date of Patent: Jun. 16, 2026

(54) USE OF ARTIFICIAL INTELLIGENCE ("AI") TO DETECT THE EXPRESSION OF CYTOKERATIN 17 IN UROTHELIAL CELLS FROM PATIENTS' VOIDED URINE

(71) Applicant: Acupath Laboratories, Inc., Plainview, NY (US)

(72) Inventors: Michael Matthews, Baldwin, NY (US); Brian Kunkel, Huntington, NY (US); John Cucci, Saint James, NY (US); Thomas M. Dewar, Yonkers, NY (US)

(73) Assignee: ACUPATH LABORATORIES, INC., Plainview, NY (US)

( * ) Notice: Subject to any disclaimer, the term of this patent is extended or adjusted under 35 U.S.C. 154(b) by 0 days.

(21) Appl. No.: 19/088,701

(22) Filed: Mar. 24, 2025

(65) Prior Publication Data

US 2025/0299332 A1      Sep. 25, 2025

Related U.S. Application Data

(60) Provisional application No. 63/568,968, filed on Mar. 22, 2024.

(51) Int. Cl.
*G06T 7/00* (2017.01)
*G06V 10/764* (2022.01)
(Continued)

(52) U.S. Cl.
CPC .......... *G06T 7/0012* (2013.01); *G06V 10/764* (2022.01); *G06V 20/698* (2022.01);
(Continued)

(58) Field of Classification Search
None
See application file for complete search history.

(56) References Cited

U.S. PATENT DOCUMENTS 11,360,092 B2      6/2022  Shroyer
2020/0284794 A1*  9/2020  Shroyer .................. G01N 33/48
(Continued)

FOREIGN PATENT DOCUMENTS

WO      WO2018/027091      2/2018

OTHER PUBLICATIONS

Bencze, János, et al. "Comparison of semi-quantitative scoring and artificial intelligence aided digital image analysis of chromogenic immunohistochemistry." Biomolecules 12.1 (2021): 19. (Year: 2021).*
(Continued)

*Primary Examiner* — Samah A Beg
(74) *Attorney, Agent, or Firm* — Jacob Baldinger, PLLC

(57) ABSTRACT

Conventional, manual identification and scoring of a whole slide image (WSI) to detect Cytokeratin 17 (K17) expression has limitations in terms of lower accuracy in the medium grade cases, slower turn-around time, and high inter and intra-observer variability. Each WSI can take a pathologist six to ten minutes to examine. This is because the brown color staining indicating the presence of K17 may be one of thousands or tens of thousands or other expressions present on the slide. Apparatus and methods are provided for an artificial intelligence (AI) solution that identifies and quantifies positively stained urothelial cells in WSI of urine cytology to aid the diagnosis of urinary bladder carcinoma. An illustrative AI solution may include one or computer models that are programmed to run one more machine learning (ML) models. The ML models may be trained to recognize subtle and complex patterns and features associated with specific diseases.

17 Claims, 18 Drawing Sheets
(15 of 18 Drawing Sheet(s) Filed in Color)

(51) Int. Cl.

| | | |
|---|---|---|
| *G06V 20/69* | (2022.01) |
| *G16H 10/40* | (2018.01) |
| *G16H 10/60* | (2018.01) |
| *G16H 50/30* | (2018.01) |

(52) U.S. Cl.
CPC ............. *G16H 10/40* (2018.01); *G16H 10/60* (2018.01); *G16H 50/30* (2018.01); *G06T 2207/10056* (2013.01); *G06T 2207/20081* (2013.01); *G06T 2207/30024* (2013.01)

(56) References Cited

U.S. PATENT DOCUMENTS

| | | | | |
|---|---|---|---|---|
| 2024/0062372 | A1* | 2/2024 | Sue | G16H 30/40 |
| 2024/0233123 | A1* | 7/2024 | Kang | G16H 15/00 |

OTHER PUBLICATIONS

Pantanowitz, Liron, et al. "Artificial intelligence-based screening for Mycobacteria in whole-slide images of tissue samples." American Journal of Clinical Pathology 156.1 (2021): 117-128. (Year: 2021).*

Zhang, Zhihui, et al. "Developing a machine learning algorithm for identifying abnormal urothelial cells: a feasibility study." Acta Cytologica 65.4 (2021): 335-341. (Year: 2021).*

Sruthi Babu, et al., Validation of a Novel Cytologic Biomarker for Urothelial Carcinoma, Poster Session Presented at the American Association for Cancer Research on May 20, 2019.

Liwu Guo, et al., Acu-URO17 Is a Highly Sensitive and Specific Bladder Cancer Biomarker, Acupath Laboratories, Sep. 2023.

Usman Khalid, et al., Artificial Intelligence Algorithms and Their Current Role in the Identification and Comparison of Gleason Patterns in Prostate Cancer Histopathology: A Comprehensive Review, Diagnostics 2024, 14, 2127, also available at: https://doi.org/10.3390/diagnostics14192127, Sep. 25, 2024.

Sruthi Babu, et al., Keratin 17 Is a Novel Cytologic Biomarker for Urothelial Carcinoma Diagnosis, Am J Clin Pathol 2021; XX:1-0, also available at: https://academic.oup.com/ajcp/advance-article/doi/10.1093/ajcp/aqab050/6291910, Jun. 2021.

Madeleine S. Durkee, et al., Artificial Intelligence and Cellular Segmentation in Tissue Microscopy Images, Am J Pathol 2021, 191:1693-1701, also available at: https://doi.org/10.1016/j.ajpath.2021.05.022, Oct. 2021.

Sruthi Babu, et al., Keratin 17 is a sensitive and specific biomarker of urothelial neoplasia, Modern Pathology, vol. 32, Issue 5, 717-724, United States & Canadian Academy of Pathology, also available at: https://doi.org/10.1038/s41379-018-0177-5, Nov. 15, 2018.

Nikhil Vasdev, et al., The role of URO17™ biomarker to enhance diagnosis of urothelial cancer in new hematuria patients—First European Data, BJUI Compass, 2021, 2:46-52, Jan. 2021.

Liwu Guo, et al., Acu-URO17 is a highly sensitive and specific bladder cancer biomarker, BJUI Compass. 2024,1-5, Feb. 29, 2024.

William T. Tran, et al., Personalized Breast Cancer Treatments Using Artificial Intelligence in Radiomics and Pathomics, Journal of Medical Imaging and Radiation Sciences 50 (2019) S32-S41, Dec. 2019.

Ruslan Salakhutdinov, Tutorial on Deep Learning, "Deep Learning I Supervised Learning," The Simons Institute for the Theory of Computing, also available at: https://www.cs.cmu.edu/~rsalakhu/talk_Simons_part1_pdf.pdf, Jan. 26, 2017.

Nikhil Vasdev, et al., The role of URO17™ biomarker to enhance diagnosis of urothelial cancer in new hematuria patients—First European Data, BJUI Compass. 2020;00:1-7. Oct. 2020.

* cited by examiner

FIG. 1

| CYTOLOGY | N | URO17 EXPRESSION (TOTAL) | URO17 HIGH EXPRESSION | URO17 LOW EXPRESSION | URO17 NEGATIVE |
|---|---|---|---|---|---|
| CANCER | 9 | 9 (100%) | 9 (100%) | 0 (0%) | 0 (0%) |
| SUSPICIOUS | 31 | 31 (100%) | 27 (87%) | 4 (13%) | 0 (0%) |
| ATYPICAL | 145 | 129 (89%) | 93 (64%) | 36 (25%) | 16 (11%) |
| NEGATIVE | 1423 | 167 (12%) | 51 (4%) | 116 (8%) | 1256 (88%) |

FIG. 2

| CYTOLOGY | N | URO17 EXPRESSION (TOTAL: H+L) | URO17 HIGH EXPRESSION | URO17 LOW EXPRESSION | URO17 NEGATIVE |
|---|---|---|---|---|---|
| CANCER | 20 | URO17: 20 (100%)<br>FISH-POS : 15 (75%)<br>FISH-NEG : 5 (25%) | TOTAL: 20 (100%)<br>FISH-POS : 15 (75%)<br>FISH-NEG : 5 (25%) | TOTAL: 0 (0%)<br>FISH-POS : 0 (0%)<br>FISH-NEG : 0(0%) | TOTAL: 0 (0%)<br>FISH-POS : 0 (0%)<br>FISH-NEG : 0 (0%) |
| SUSPICIOUS | 51 | URO17: 50 (98%)<br>FISH-POS : 21 (41%)<br>FISH-NEG : 30 (59%) | TOTAL: 44 (86%)<br>FISH-POS : 19 (37%)<br>FISH-NEG : 25 (49%) | TOTAL: 6 (12%)<br>FISH-POS : 2 (4%)<br>FISH-NEG : 4 (8%) | TOTAL: 1 (2%)<br>FISH-POS : 0 (0%)<br>FISH-NEG : 1 (2%) |
| ATYPICAL | 456 | URO17: 373 (82%)<br>FISH-POS : 48 (11%)<br>FISH-NEG : 325 (71%) | TOTAL: 257 (56%)<br>FISH-POS : 39 (9%)<br>FISH-NEG : 218 (49%) | TOTAL: 116 (25%)<br>FISH-POS : 9 (2%)<br>FISH-NEG : 107 (23%) | TOTAL: 83 (18%)<br>FISH-POS : 5 (1%)<br>FISH-NEG : 78 (17%) |
| NEGATIVE | 1718 | URO17: 569 (33%)<br>FISH-POS : 16 (1%)<br>FISH-NEG : 553 (32%) | TOTAL: 156 (9%)<br>FISH-POS : 4 (0.2%)<br>FISH-NEG : 152 (8.8%) | TOTAL: 413 (24%)<br>FISH-POS : 12 (0.7%)<br>FISH-NEG : 401 (23%) | TOTAL: 1149 (67%)<br>FISH-POS : 0.7 (1%)<br>FISH-NEG : 1139 (66.3%) |

FIG. 3
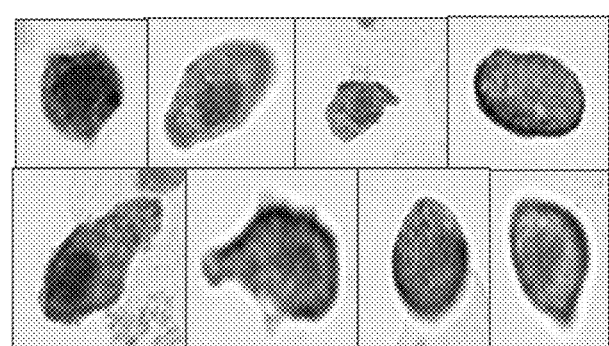
Right Panel
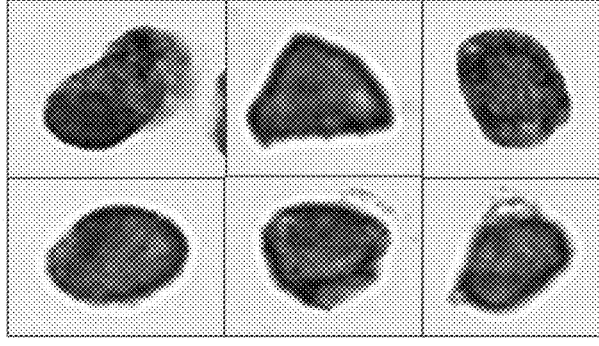
Middle Panel
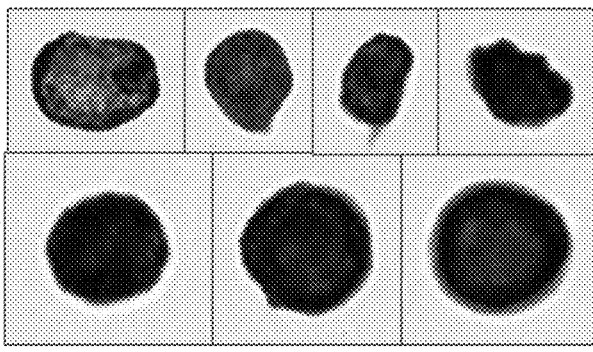
Left Panel

Highly stained / precipitates    Light Blushing    Neutrophils

Folds    Irregular Shaped    Non-visible Nucleus

FIG. 7A
Previous Count - HC - 20; LC - 50; Pathologist - 0.
New Count- HC - 11; LC - 7
Negative Samples
Positive Samples - HC/LC
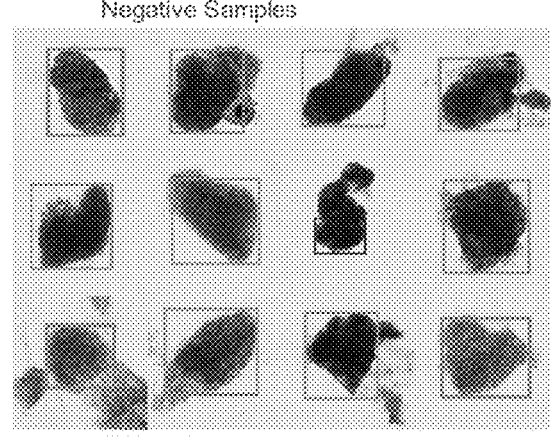
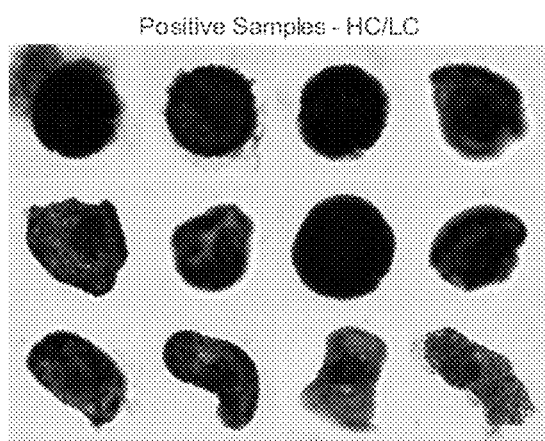
FIG. 7B
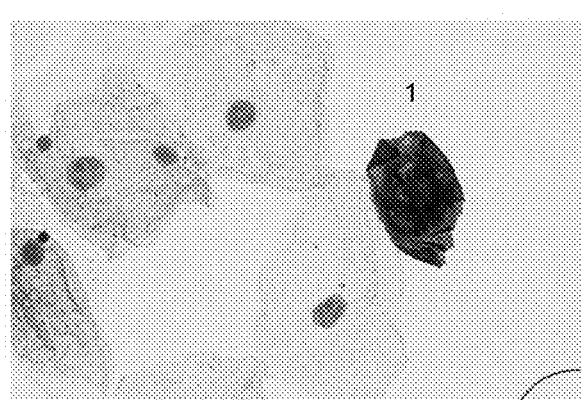
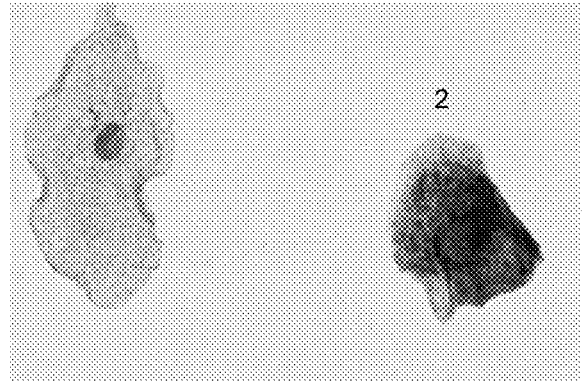

FIG. 9
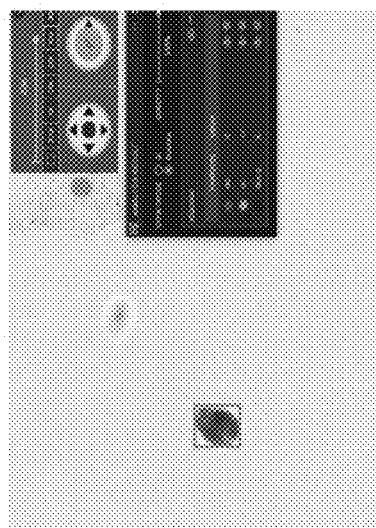
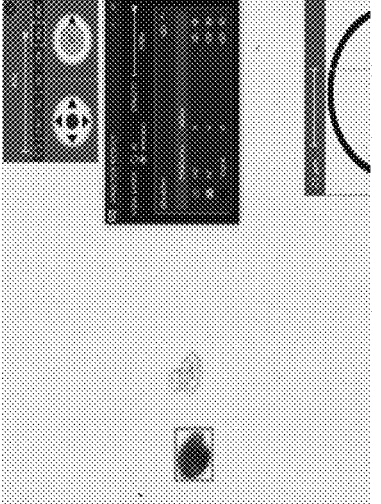
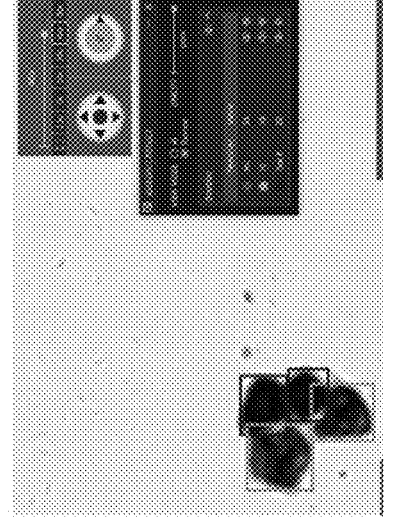
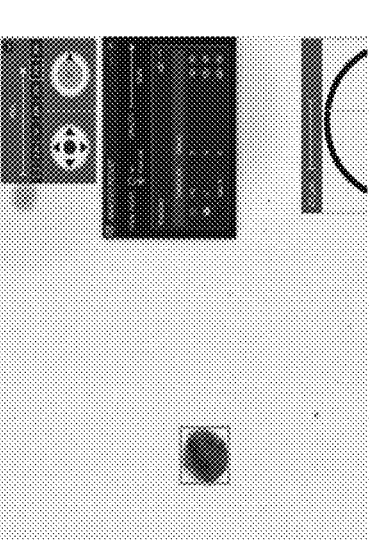
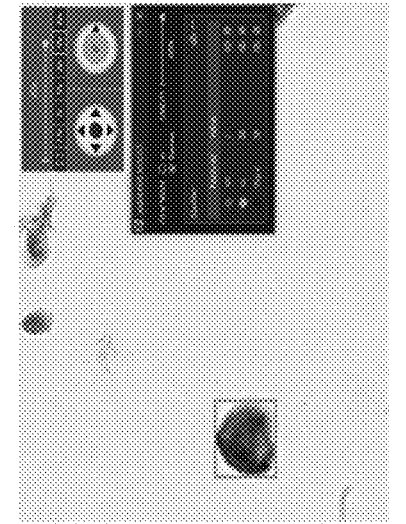

FIG. 13

| PHYSICIAN:   IMA TEST, M.D<br>ABC SURGERY<br>123 MAIN STREET, Suite: 12345<br>NEW HYDE PARK, NY 11040<br>Acct #   1433-2010-1    ☎ (123) 456-7890    Rte 15 | PATIENT:   TEST URO TEST              DOB:<br><br>Acct#:   2382924<br>Age:<br>Sex: |
|---|---|

URINE CYTOLOGY

● DIAGNOSIS: ATYPICAL FINDINGS

Specimen consists of rare detached degenerated and atypical urothelial cells showing ground-glass and/or reticulated chromatin pattern, suggestive of polyoma virus infection.

URO17 EXPRESSION:

● HIGH                                           Number of positive cells:   | 30 |

Probability of urothelial cancer is elevated.   Additional testing and diagnostic workup is recommended. Acupath URO17 results should be utilized in conjunction with urine cytology results and other known clinical risk factors to further stratify overall risk of urothelial cancer.

URO17 SCORING CRITERIA

| Diagnosis Categories | Number of stained urothelial cells |
|---|---|
| Negative | 0 - 4 |
| Low Expression | 5 - 19 |
| High Expression | ≥ 20 |

GROSSING

Adequacy: Satisfactory For Evaluation.
Specimen Type: Urine, Voided
Gross Description: Rec'd 30ml of fixed yellow urine in Thin Prep vial. Prepared 1 Thin Prep slide. Performed 1 URO17.

Disclaimer:
Specimen was tested using the Keratin 17 (K17) mouse monoclonal antibody KDX 1-1032 A Anti-Keratin 17, with appropriate positive and negative controls as required by ASCO-CAP guidelines. Prior urothelial trauma or treatment for bladder cancer may cause potentially false- positive Acupath URO17 results. Expected normal range = Negative. This test was developed and its performance characteristics determined by Acupath Laboratories , Inc., certified under the Clinical Laboratory Improvement Amendments of 1988 (CLIA) as qualified to perform high complexity testing. It has not been cleared or approved by the US Food and Drug Administration.

USE OF ARTIFICIAL INTELLIGENCE ("AI") TO DETECT THE EXPRESSION OF CYTOKERATIN 17 IN UROTHELIAL CELLS FROM PATIENTS' VOIDED URINE

PRIORITY DATA

This application is a nonprovisional of U.S. Provisional Application No. 63/568,968, filed on Mar. 22, 2024, which is hereby incorporated herein by reference in its entirety.

FIELD OF TECHNOLOGY

This disclosure relates to apparatus and methods for an artificial intelligence (AI) diagnostic solution that identifies and quantifies positively stained urothelial cells in whole slide images of urine cytology to aid the diagnosis of urinary bladder carcinoma.

BACKGROUND

Annually, there are over 197,000 new diagnoses of bladder cancer in Europe, 85,000 in the United States and 430,000 globally. These numbers place bladder cancer as the fourth most prevalent malignancy in men and the fifth most prevalent in women. According to the American Cancer Society, in the United States, as of 2023 bladder cancer is the fourth most frequent cancer in men (approximately 62, 420 new cases annually) and although less frequent in women (approximately 19, 870 new cases annually), women are often diagnosed at a later, more advanced stage of the disease.

Bladder cancer typically originates in urothelial cells that line the inside of the entire urinary tract. Urothelial cells are unique in that they can stretch and contract, which is essential for the function of the urinary tract.

Early detection is crucial for improving clinical outcomes. Urothelial cancers ("UC") account for ~95% of diagnosed bladder cancers and most cases are diagnosed as Non-Muscle Invasive Bladder Cancer (NMIBC) which provides a more curable prognosis. NMIBC cases have a high recurrence rate of 80% in high-risk lesions and up to 50% in low-risk lesions. Nonetheless, the 5-year survival rate is 94% if detected early. For patients with UC, clinical guidelines recommend cystoscopies performed in 3-month intervals during the first 2 years, 6-month intervals the following 2 years, and then once every year. Accordingly, lifelong surveillance is an important part of routine management for patients with bladder cancer.

Cystoscopy, in combination with voided urine cytology and upper urinary tract imaging, plays a key role in the surveillance of the recurrence of bladder cancer as well as detection of new UC in hematuria patients. Cystoscopy is an invasive procedure that involves inserting a thin, lighted tube (cystoscope) through the urethra and into the bladder. It allows the practitioner to visually inspect the inside of the bladder for any abnormal areas or growths. During a cystoscopy, if suspicious area is observed, the practitioner can pass a small instrument through the cystoscope to collect a tissue sample (biopsy). This tissue sample is then sent to a laboratory for examination under a microscope to determine if cancer cells are present.

Another invasive test, such as a retrograde pyelogram may be used to detect bladder cancer. The retrograde pyelogram includes inserting a catheter into the ureters (tubes that connect the kidneys to the bladder) and injecting dye for subsequent x-ray imaging. X-rays are then taken, which allows a practitioner to visualize the urinary tract and identify any abnormalities.

Currently, invasive imaging, cystoscopy and associated biopsies remain the most definitive method for detecting bladder cancer. However, the utilization of invasive imaging and cystoscopy is often not effective in detecting smaller lesions. Frequently, cystoscopy is associated with complications such as urinary tract infection, and hematuria, even morbidity. Urothelial cells line the entire urinary tract, and tumors can occur in multiple locations, and in areas other than the bladder itself—wherever urothelial cells are found-making it challenging to identify all problematic areas.

Non-invasive urine cytology is widely used as a noninvasive method for screening and surveillance of bladder cancers. Although it is highly specific (~90%) for the detection of UC, it has low sensitivity (~48%) for the detection of UC, especially for low-grade UC where it misses over half of the cases. Furthermore, reactive cellular changes associated with infection or inflammation can also induce cellular atypia, mimicking high-grade UC that could contribute to the general inaccuracy of urine cytology. The recent introduction of the Paris system for urine cytology tried to facilitate the interpretation of the cytology results but the clinical implications of "Suspicious" and "Atypical" categories are still not clearly defined which causes significant confusion for physicians.

Currently, many of the patients may be required to undergo painful and expensive invasive procedures even though they may not have active UC. One of the first symptoms of bladder cancer includes hematuria or blood in the urine. To improve curable prognoses, typically an invasive cystoscopy is performed on a substantial portion of hematuria patients even though most of these patients may not have UC. For example, other noncancerous reasons for hematuria include urinary tract infections, kidney stones, kidney diseases (such as glomerulonephritis or polycystic), prostate problems (benign prostatic hyperplasia or prostatitis), injuries, medication, and strenuous exercise. Invasive procedures are associated with higher risk of infection, complications, pain and discomfort.

A non-invasive, less expensive and accurate test that could determine who requires, and as importantly, who does not require cystoscopy follow-up is a significant clinical need in the management and diagnosis of UC. Currently, there are several noninvasive urinary biomarker tests commercially available, including the UroVysion™ FISH test. The UroVysion™ FISH test looks for an abnormal number of chromosomes (aneuploidy) in cells found in urine samples. The UroVysion™ FISH test specifically targets chromosomes 3, 7, and 17, and the 9p21 locus (where the p16 tumor suppressor gene is located). FISH Technology uses fluorescently labeled DNA probes that bind to specific DNA sequences on chromosomes. If there are abnormalities in the number of copies of these chromosomes or in the 9p21 locus, the fluorescent signals will be abnormal, indicating the presence of potentially cancerous cells.

While the UroVysion FISH test offers valuable insights, it has potential downsides. Interpreting FISH results can sometimes be complex, and variations in interpretation can occur. FISH testing is also relatively expensive compared to standard urine cytology. FISH testing requires specialized equipment and trained personnel to perform and interpret the results accurately. The high cost of FISH testing limits its accessibility and availability.

Furthermore, FISH testing, although helpful, may not detect low-grade tumors. It is designed to detect specific chromosomal abnormalities, and not all bladder cancers exhibit these particular changes. Other notable biomarkers of bladder cancer include nuclear matrix protein NMP-22, BTA stat, and BTA TRAK. However, most of these available urinary markers also lack sensitivity in detecting early-stage UC, and the clinical evidence still does not appear to support the widespread application of the tests in clinical settings.

Early detection of UC is critical. Prognosis and mortality are strongly correlated with cancer staging at the time of diagnosis. A cancer may be confined to the inner lining of an organ or may progress to the point where it has invaded muscle. However, when cancer has invaded the muscle, the cancerous cells have penetrated deeper into the muscle tissue. Muscle invasion in the case of bladder cancer, this means the cancer has grown into the detrusor muscle, which is the thick muscle in the bladder wall.

Urothelial cancers account for ~95% of diagnosed bladder cancers, and most cases are diagnosed as NMIBC, which provides a more favorable prognosis. After a cancer has invaded the muscle result in significant increases in mortality. Unfortunately, 37% of new bladder cancer cases are found to have muscle-invasive malignancies at the time of diagnosis. This late-stage diagnosis can result in a 60% five-year survival rate, dropping to 4% for metastatic malignancy. On the other hand, the 5-year survival rate is 94% if detected early. These statistics underscore the importance of early UC detection, diagnosis and timely treatment.

Accordingly, it would be desirable to further enhance the reliability and accuracy of noninvasive biomarker tests for UC and reduce the frequency of invasive detection methods. It is also desirable to reduce the costs associated with noninvasive UC testing and increase the availability of accurate noninvasive testing. Accordingly, it is desirable to provide APPARATUS AND METHODS FOR USE OF ARTIFICIAL INTELLIGENCE ("AI") (TO DETECT THE EXPRESSION OF CYTOKERATIN 17 IN UROTHELIAL CELLS FROM PATIENTS' VOIDED URINE.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The objects and advantages of the disclosure will be apparent upon consideration of the following detailed description, taken in conjunction with the accompanying drawings, in which like reference characters refer to like parts throughout, and in which:

FIG. 1 shows illustrative research data;
FIG. 2 shows illustrative research data;
FIG. 3 shows illustrative microscopic images;
FIG. 7A shows illustrative microscopic images;
FIG. 7B shows illustrative microscopic images;
FIG. 9 shows illustrative microscopic images.

FIG. 13 shows an illustrative pathology report.

DETAILED DESCRIPTION

Figure 4A:
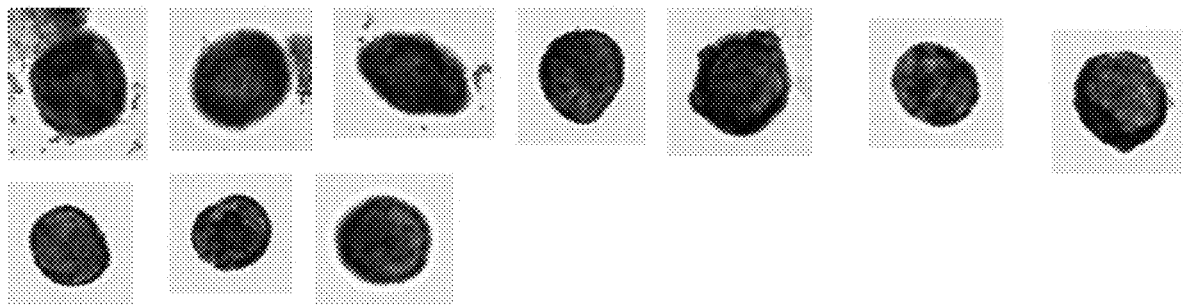
FIG. 4A shows illustrative microscopic images.

Typically, patients that have observed some form of hematuria visit their urologist. During the initial office visit, the urologist performs a quick in office dip stick test to confirm the presence of blood in the urine. The urologist then sends the patient for a cytology test. A pathologist reviews the cells captured during the cytology test under a microscope and looks for changes in the presentation of the cells (morphology) or other atypical characteristics. For example, pathologists may look for morphological changes such as alterations in the shape, size, and structure of the cells. Morphological changes may include atypical presentation of cells such as clusters of cells that come off in sheets from the bladder wall.

Observable morphological changes are typically late-stage indicators. By the time the pathologist observes morphological changes, any detected cancer is probably already established. Non-invasive early detection of UC can be difficult, as visible cellular changes occur relatively late in the disease process. Accordingly, current clinical methods may guide a urologist to recommend an invasive cystoscopy procedure if there are any atypical cytology results and the patient has presented with blood in the urine. However, even the results of early cystoscopy testing are typically negative. If there is cancer developing, it is likely too early to be detected by cystoscopy testing.

It has been theorized that subtle, molecular or genetic changes may precede visible morphological changes. Exploration of Cytokeratin 17 (K17) as a biomarker associated with detection of those subtle changes has been recently investigated. K17 is an oncoprotein normally expressed in stem cells of embryonic ectoderm, skin appendages, and the endocervical mucosa, but not in most normal mature epithelia, and is thought to be involved in tissue regeneration and repair. K17 functions as an oncoprotein by regulating the subcellular localization and degradation of p27KIP1, influencing cervical cancer pathogenesis. This has suggested that keratins overexpressed selectively in human carcinomas may offer diagnostic and prognostic utility.

Recent studies confirmed that K17 showed extremely high sensitivity (80-100%) and high specificity (86-96%) on selected urine specimens from urothelial carcinoma from both recurrent UC and new UC from hematuria patients. K17 is typically expressed during embryonic development, silenced in most adult somatic tissues, and re-expressed in a range of cancer types. K17 was expressed in 100% of UCs but not in normal urothelial mucosa. Furthermore, K17 immunocytochemistry (ICC) is 100% sensitive and 96% specific as a cytologic biomarker for UC. Testing for K17 biomarker expression may help risk-stratify those patients that would likely develop UC verses those patients that may have hematuria for other reasons (e.g., kidney stones or urinary tract infections). The expression of K17 indicates changes within the cytoskeleton (part of the cell that helps regulate cell proliferation). Observing these changes in the cytoskeleton helps a practitioner decide if there is a higher likelihood for a patient to develop UC.

Based on recent research associated with the K17 biomarker, Acupath Laboratories, Inc. of Plainview, New York (Acupath) developed its Acu-URO17 test. Acu-URO17 is a highly sensitive and specific immunocytochemistry (ICC) test for the detection of K17, a biomarker commonly expressed in bladder cancer cells. Acupath is leading investigation of testing methods using K17 expression and has recently conducted a large-scale comparison of Acu-URO17, urine cytology, and UroVysion™ FISH tests on 2,378 voided urine specimens.

On urine cytology cases that yielded high-grade urothelial cancer diagnoses, Acu-URO17 had a sensitivity of 96% and a specificity of 82%. Furthermore, when compared to UroVysion™ FISH results, Acu-URO17 had a sensitivity of 97.1% and a specificity of 77.8% while UroVysion™ FISH had a sensitivity of 57.1% and a specificity of 77.2%. Significantly, Acu-URO17 demonstrated a high negative predictive value (NPV) of 99.9%, thus helping to both confirm negative urine cytology results (offsetting cytology's low sensitivity) and adjudicate/risk-stratify atypical and suspicious urine cytology results.

Acupath's large-scale prospective study results confirm that Acu-URO17 is a clinically relevant, non-invasive, and cost-effective tool to be used in conjunction with both urine cytology and UroVysion™ FISH in the diagnosis and management of UC.

Urine cytology has generally poor performance in detecting UC, especially low-grade UC. In the early stage of carcinogenesis, cytology tests will likely not be able to identify these cells since they may have not yet morphologically changed significantly. In comparison, these initiated or promoted cells still express K17. Therefore, Acu-URO17 test can detect them reliably even in morphologically normal cells.

In addition to the sensitivity and specificity, Acu-URO17 has a negative predictive value (NPV) of 99.90%. NPV is the probability that a person with a negative test result truly does not have the disease or condition being tested for. The 99.90% NPV strongly demonstrates that Acu-URO17 can reliably detect truly "benign" specimens as negative since K17 is not expressed. The 99.90% NPV carries an important value to accurately assure that negative results can help rule out the possibility of UC.

Although the extremely sensitive and specific Acu-URO17 test can function as a reliable auxiliary test to surveil the recurrence and even provide initial detection of bladder cancer cells in voided urine, further enhancements are desirable. Acu-URO17 is an ICC test, a laboratory technique that uses antibodies to detect specific antigens (proteins or other molecules) within cells. ICC allows researchers and clinicians to visualize the presence and location of particular molecules inside individual cells.

After applying the K17 biomarker, Acu-URO17 results may include stained urothelium cells that show discoloration evidencing varying levels of K17 expression. This discoloration is typically brownish, and the presence of the discoloration indicates that the urothelium cells are under duress. The presence of K17 expression does not confirm that the discolored urothelium cells are cancerous. However, in the absence of any other causes of urothelium duress (e.g., kidney stones, radiation therapy, UTI, and/or Bladder washing), urothelium cells expressing high levels of K17 (e.g., strong, intense discoloration) can be considered a precursor to UC progression. Strong detection of K17 in five or more urothelial cells is typically considered a positive indicator of UC and an indicator of urothelium duress.

ICC testing relies on the highly specific binding of antibodies to their target antigens. The selected antibodies are designed to recognize and bind to the specific target molecule to detect that target molecule. To make the bound antibodies visible, they are typically linked to a detectable label, such as fluorescent dyes (leading to fluorescence microscopy) or enzymes that produce a colored reaction. These labels allow the location and amount of the target antigen to be visualized under a microscope. ICC is performed on individual cells or cell cultures. Cells are typically fixed to preserve their structure and then treated to allow the antibodies to access the intracellular antigens.

However, ICC results, any many other manually applied laboratory techniques, are vulnerable to interpretive variance and error. This vulnerability stems from the multiple steps involved in the process, each of which requires precision and careful execution to achieve consistent results. Different pathologists may examine the same specimen and reach different diagnostic conclusions. Such discordance by different cytopathologists is a serious concern with wide-ranging implications.

For example, a false negative diagnosis might lead to a missed opportunity for timely intervention, allowing a disease to progress. Conversely, a false positive diagnosis could result in unnecessary and potentially harmful treatments, causing anxiety and impacting the patient's quality of life. Discordance often necessitates further investigations, such as additional biopsies, molecular testing, or second opinions. This can delay definitive diagnosis and treatment, increase healthcare costs, and prolong patient anxiety. Inter-observer variability underscores the need for more objective and automated diagnostic tools, such as artificial intelligence powered analysis algorithms, to assist pathologists and improve consistency.

Additionally, sample preparation is vulnerable to human error. Improper fixation can alter or destroy the target antigens, leading to inaccurate results. Inconsistent sectioning can affect the uniformity of applied staining. Inadequate or excessive permeabilization can hinder or enhance antibody access.

Antibody handling is another process that is vulnerable to error. Incorrect antibody dilutions can result in weak or overly strong staining. Improper antibody storage can degrade their effectiveness. Uneven application of antibodies can lead to inconsistent staining. Staining is another step in the ICC process that is vulnerable to error. Insufficient washing can lead to background staining, while excessive washing can remove bound antibodies. Incorrect incubation times can affect the intensity and specificity of staining. The use of degraded or contaminated reagents can compromise results.

Microscopy and interpretation are also procedures that are vulnerable to error. Interpreting staining results can be subjective, especially in cases of weak or ambiguous staining. Incorrect microscope settings or image processing can alter the appearance of staining. Documentation errors in recording results, or labeling samples may also cause a misdiagnosis.

There are numerous additional factors that increase the vulnerability of ICC to interpretive errors. Variations in protocols and reagents between laboratories can further increase the risk of interpretive errors. Inadequate training of personnel can lead to mistakes in any of the steps involved. High workloads and fatigue of pathologists can exacerbate the likelihood of errors.

Furthermore, manual identification and scoring of Acu-URO17 test results has limitations in terms of lower accuracy in the early-stage disease detection, disease, medium grade cases, slower turn-around time, and high inter and intra-observer variability. Each slide can take a pathologist six to ten minutes to examine. This is because the brown color staining indicating the presence of K17 may be one of thousands or tens of thousands or other expressions present on a slide.

Additionally, at 4× magnification, cells on a slide are visible to a trained eye. At 10× magnification, a trained pathologist can detect target expressions. Detecting K17 expression typically requires 20× magnification. At this level of magnification, only a relatively small number of cells are visible, requiring more pathologist time to examine and tally all K17 expressions on the slide.

Additionally, the color that typically indicates expression of K17 (typically brownish) may vary from cell to cell. Some cells may be light brown. Some cells may be dark brown. Some cells may appear almost black. Some cells may only exhibit brown at the periphery or outer perimeter. Thus, detecting the level of K17 expression requires careful scrutiny of the entire slide by a trained pathologist. Careful scrutiny of the slide requires extensive pathologist time.

Moreover, the color (or lack thereof) indicating K17 expression may vary based on slide preparation techniques and volume of cells on the slide. For example, slides prepared using a first ICC platform may result in a first shade of brown and slides prepared using a second ICC platform may result in a second shade of brown.

Thus, in addition to being challenging for a pathologist to detect, assessments of K17 expression may be associated with a high degree of observer variance. Accordingly, the current manual identification and scoring system has limitations in terms of lower accuracy in the medium grade cases, slower turn-around time, and high inter and intra-observer variability.

In addition to ICC, The level of K17 expression may also be measured by other laboratory techniques, such as immunohistochemistry (IHC), quantitative reverse transcription polymerase chain reaction (qRT-PCR), northern blotting, western blotting, enzyme-linked immunosorbent assay (ELISA), microarray analysis, or mass spectrometry. K17 expression may be detected by a solution phase protein assay (e.g., EUSA, microfluidics, flow cytometry). K17 expression may be determined by the detection of fluorescently labeled cells by flow cytometry or microfluidic based detection methods. The level of K17 expression is determined by detecting the presence of K17 mRNA or protein in a sample. In some embodiments, any amount of K17 mRNA or protein detected in the sample is correlated with a diagnosis of bladder cancer. In other embodiments, the amount of K17 protein or mRNA in a sample must exceed a threshold amount.

K17 expression may be determined by immunohistochemical staining of a urine sample that includes a detectable number of urothelial cells. Cell discoloration due to staining may indicate the strength or increased level of K17 expression. Typically, urothelial cells that express high levels K17 will exhibit darker discoloration. K17 staining is faintly detectable in benign bladder mucosa and highly expressed in diagnostic categories of UC.

Cell size, shape and contour are also important characteristics to be considered when evaluating levels of K17 expression. Cancerous cells often deviate from the normal size and shape of healthy cells. In the context of urothelial cells, round shape and smooth edge are indicative of higher UC risk. In fact, larger urothelial cells that are rounded and smooth are the hallmark UC indicators in voided urine.

Cytoplasmic features are also important characteristics to be considered when evaluating levels of K17 expression. The cytoplasm, the cell's jelly-like interior, can exhibit changes in density and staining patterns in the presence of biomarkers such as K17. For example, the nuclear-to-cytoplasmic (N:C) ratio is a valuable morphologic feature for the diagnosis of atypia and malignancy. In pathological conditions, such as cancer, both cell shape and the N:C ratio can be altered. Cancer cells often exhibit abnormal shapes and an increased N:C ratio, which are used as diagnostic indicators.

Typically, the presence of high N:C ratio cells in a population of cells that normally displays a low to moderate N:C ratio is a sign of cellular atypia and even malignancy. The presence of relatively large urothelial cells in a voided urine population is abnormal. Healthy individuals do not have such large morphologically abnormal cells in their voided urine.

However, it is challenging for a cytopathologist to detect urothelial cells that have an N:C ratio just at or above the threshold normal ratio of ~>0.5. Cells that are at or slightly above this normal threshold ratio may only be classified as atypical, but not on their own, as strong precursors of UC. Adding K17 staining helps determine if detected atypia is likely to progress to UC in the absence of any other causes for atypia.

A slide that includes a cellular specimen may also include other biological and nonbiological materials. It is important to determine what is a cell and what is not. Visibility of cellular structures, such as the nucleus, is an important positive cellular indicator. The nucleus, a cell's control center, can show abnormalities in size, shape, texture and increased K17 expression in a diseased cell. Visualizing the size and shape of the nucleus helps determine that what is being examined is a cell. Additionally, in the context of UC detection, the size and shape of the nucleus indicates that cell under examination or exhibiting a chromogenic stain is a urothelial cell.

For example, cells present on a slide may be overwhelmed with chromogenic stain. Cells on a slide that have a visible nucleus and the chromogenic stain, can be more confidently identified as expressing K17. The uniqueness of the K17 expression is not limited to larger morphologically abnormal cells. Even morphology of urothelial cells that would otherwise appear benign to a cytopathologist may in fact express K17. However, it is critical that the material under examination is identified as a urothelial cell as opposed to other cells or non-cellular material that may be present on a slide.

For example, the presence of "precipitate" on a slide presents challenges which interfere with accurate microscopic examination. Precipitate may include unwanted solid particles that form within staining solutions. These particles can then adhere to cell samples on slides, creating artifacts that interfere with accurate microscopic examination. The presence of precipitate can obscure cellular details and make it difficult to distinguish between true pathological findings and artifacts. This can lead to misinterpretations and potentially inaccurate diagnoses.

The presence of precipitate is a troublesome artifact that pathologists and cytotechnologists must be aware of to ensure accurate interpretation of cell samples. Cytology relies heavily on staining techniques to highlight cellular components. If the staining solutions are not properly maintained, they can form precipitates. These precipitates appear as small, irregular particles on the slide, which can be mistaken by a cytologist for bacteria, cellular debris, or other diagnostically significant features.

As a result of the various diagnostic uncertainties, it is challenging for cytopathologists to accurately, consistently and uniformly identify and classify urothelial cells that express K17 to a confidence level that requires intervention to treat UC. Although the Acu-URO17 is a clinically relevant, non-invasive, and cost-effective ICC test to be used for early diagnosis of UC, it is vulnerable to interpretive discordance and other errors. Interpretive discrepancies or even inconsistencies may necessitate further investigations, such as additional biopsies, molecular testing, or second opinions. This can delay definitive diagnosis and treatment, increase healthcare costs, and prolong patient anxiety.

To enhance the efficacy of the Acu-URO17 test, and to implement measures to minimize vulnerability of the Acu-URO17 test to interpretive error or discordance, apparatus and methods for use of artificial intelligence (AI) to detect the expression of K17 in urothelial cells are provided. It would be further be desirable to utilize AI to perform accurate, reliable and cost-effective examination of immunohistochemical staining for threshold amounts of K17 expression in urothelial cells.

Apparatus and methods are provided for an AI platform that reliably identifies and quantifies positively stained urothelial cells in whole slide images (WSI) of urine cytology. The AI engine described herein aids the early detection and diagnosis of UC.

An AI engine for identifying and quantifying positively stained urothelial cells in WSIs of urine cytology samples to aid the diagnosis of urinary bladder carcinoma is provided. The AI engine may include one or computer processors that are programmed to run one more machine learning (ML) models. The AI engine may perform other functions in response to diagnostic analysis received from the ML model. For example, the AI engine may generate annotations highlighting areas or cells in a WSI for consideration by a trained cytopathologist. The AI engine may consistently and reproducibly annotate WSIs, reducing discordance rates for examination of WSIs.

The AI engine may include a modular architecture, allowing for flexibility and the integration of new models and data sources over time. Illustrative components include a data ingestion and preprocessing module. This module may include software and hardware that handles the intake of various medical data formats, including WSIs from pathology, Electronic Health Records (EHR) data such as patient demographics, medical history, lab results, medications, and procedure codes, and Unstructured Data such as Clinical notes, radiology reports, and pathology reports in natural language format. The data ingestion and preprocessing module may perform preprocessing steps like data cleaning, normalization, anonymization, and feature extraction tailored to each data type. For instance, image data might undergo noise reduction and augmentation.

The AI engine may include an inference and interpretation module. This module may include software and hardware for receiving the outputs from the machine learning models core (described below) and synthesizing those outputs into a coherent and interpretable diagnostic suggestion. For example, it may consider the confidence scores of a suite of ML models and apply clinical rules and knowledge to refine the final diagnostic output. This module might also provide explanations for the AI engine's reasoning, highlighting the key features or evidence that led to its conclusion.

The AI engine may include a user interface and reporting module. This module may include software and hardware that provides a user-friendly interface for medical professionals to interact with the AI engine. The user interface and reporting module may allow users to input patient data and WSIs. The module may allow users to visualize the AI engine's analysis, review the supporting evidence, and have an opportunity to reach their own diagnostic decisions regarding a WSI based on output of the AI engine. This module may also generate reports summarizing the AI engine's findings and the reasoning behind them. For example, the inference and interpretation module may generate a visual overlay showing areas of interest within a WSI.

The AI engine may include a machine learning model core. The machine learning core may include one or more machine learning (ML) models, and associated software and hardware, for performing diagnostic tasks. A ML model utilized by the AI engine may be a computer program that has been trained to recognize patterns in data and then use those patterns to make predictions or decisions about new, unseen data. Instead of being explicitly programmed with rules, a ML model "learns" from data. This learning process involves feeding the model large amounts of training data and allowing it to learn and then identify underlying relationships and patterns in the new data.

ML models may be trained on vast datasets of digital pathology images, allowing them to recognize subtle and complex patterns and features associated with specific diseases. An ML model can be trained to analyze cell features such as level of K17 expression, external size/shape, and the presence and size of cellular structures.

The AI engine may provide high throughput, standardized, quantitative analysis of microscopic cytopathology images. The relevant quantitative information may be extracted from image data sets of pathological specimens. Illustrative quantitative information may include cell size, shape, staining intensity, staining uniformity, and local texture, nucleus or organelle size, outer smoothness, N:C ratio, unusual features or appearance and other cellular characteristics.

Illustrative quantitative information may include multiplexed microscopy data. Multiplexed microscopy data may include spatial distribution of multiple biological markers, such as cell surface proteins captured by immunohistochemistry analysis or immuno fluorescence. Current microscope designs and staining protocols have greatly increased the number of markers that can be captured in a given sample, allowing for co-localization of upward of 40 markers per individual frame. Highly multiplexed imaging produces rich data sets that include detailed information on phenotype and cell spacing.

The ML model may include one or more computer-visualization algorithms that are configured to identify structures and individual cells within digital quantitative information. The computer-visualization algorithms themselves include iteratively trained ML models. The computer-visualization algorithms may be configured to detect and segment urothelial cells in ex vivo tissue. The AI engine may thus provide high-throughput quantification of cell features, including cell frequency, cell morphology, cell-specific signal intensity, and spatial distribution of cells.

However, in the context of UC detection and level of K17 expression, the training of the computer-visualization algorithms is not trivial. For example, cell and cell-nucleus segmentation can be performed through segmentation semantic schemes. Quantitative characteristics acquired from these segmentations, such as nucleus-to-cytoplasm ratio, can be indicative of cancer grade. However, semantic segmentation of cells can fail in crowded regions or in images with low signal-to-noise or signal-to-background ratios.

The ML model may utilize semantic segmentation in combination with object-detection methods to generate object-level segmentation of cells rather than image-level segmentation. The combined instance segmentation may generate pixel-level segmentation of individual cells in an image. The pixel-level overlapping cells in an image, resulting in improved cell-frequency data.

The ML model may utilize generative adversarial networks (GANs). A typical GAN architecture may include two networks, a generator and a discriminator, which are trained competitively to generate a simulated version of the input image as it would present in a different context. GAN segmentation may convert an input image into the mask domain, in which each class is represented as a specific pixel value. In addition to image segmentation, image conversion can also mitigate generalizability-related problems in deep learning.

GANs may normalize staining variability across multiple institutions and multiple tissue types. Additionally, GAN architectures have been trained to rectify image artefacts, to de-noise low signal-to-noise ratio images, and to generate isotropic resolution in three dimensions.

The AI engine may provide high throughput computation of interpretable features that previously would have required costly and time-intensive manual annotation of images by a cytologist. However, selection bias, sample processing, and imaging systems may present challenges in applying AI to cell image analysis. Selection bias may relate to tissue sampling and building training, validation, and testing sets of data.

Illustrative ML models included in the AI engine may include deep learning (DL) models. DL models utilize artificial neural networks, mimicking the structure and function of the human brain. DL models, particularly convolutional neural networks (CNNs), excel at image analysis and feature recognition. In pathology, CNNs can be trained to detect specific cellular structures, shapes, and textures indicative of biomarkers.

The AI engine may include illustrative ML models such as Support Vector Machines (SVMs) and Random Forests. These models learn from labeled data to make predictions. For example, in pathology, these models can be trained to classify cells as normal or abnormal based on features extracted from digital images.

Illustrative ML models may utilize unsupervised learning techniques. Unlike supervised learning models trained with labeled data, unsupervised techniques can identify hidden patterns within large datasets. This can be useful for discovering novel biomarkers not yet fully understood. These models can analyze vast collections of pathological images and group cells with similar characteristics, potentially leading to the identification of new disease markers.

The AI solution may utilize a supervised machine learning ("SML") model. An SML is defined by its use of labeled data sets to train algorithms that classify data or predict outcomes accurately. As input data is fed into the SML model, it adjusts its weights until the model has been fitted appropriately, which occurs as part of the cross-validation process. An SML model may be trained to identify K17 expressions.

Various algorithms and computations techniques may be used in supervised machine learning processes. Possible learning methods (which may be calculated through use of programming languages like R or Python) include: Neural networks, Naive bayes, Linear regression, Logistic regression, SVMs, K-nearest neighbor, Decision tree and Random forest.

SML models may be utilized for classification tasks. Classification uses an SML model to accurately assign test data into specific categories. It recognizes specific entities within the dataset and attempts to draw conclusions on how those entities should be labeled or defined. In the context of cellular pathology, a key application of machine learning is to accurately identify structures and individual cells within images. Cell segmentation may be achieved by iterative training of AI computer-visualization algorithms. After strategical training, the AI model may then be used to predict cell segmentation in new data, allowing for high-throughput mining of quantitative descriptors of tissue pathology.

The AI engine may include computer hardware needed to run a ML model. The hardware needed can vary greatly depending on the complexity of the ML model and the size of the data it needs to process. Key components may include a Central Processing Unit (CPU). The CPU acts as the brain of the computer, handling general processing tasks. More cores and higher clock speeds generally translate to faster training and running of models, especially for tasks with a significant CPU workload. Hardware may include a Graphics Processing Unit (GPU). Often referred to as the workhorse for machine learning, GPUs are highly parallel processors designed for tasks like image and video processing. ML models heavily leverage GPUs due to their ability to handle massive amounts of calculations simultaneously.

Other hardware may include Random Access Memory (RAM) which acts as the temporary workspace for a computer system. During training and running, the model loads data and intermediate calculations into RAM. Having sufficient RAM ensures smooth operation and avoids bottlenecks. The amount of RAM needed depends on the model size and dataset, but generally, more is better. A large, fast storage drive is crucial for storing your training data and the trained model itself. Solid State Drives (SSDs) offer much faster read/write speeds compared to traditional Hard Disk Drives (HDDs), significantly improving training times when dealing with large datasets.

The objective of an AI solution is to achieve a high level of accuracy and concordance when evaluating K17 expressions and reducing the processing time to 4-5 minutes or less per slide. In an exemplary embodiment, the AI solution may reduce WSI evaluation to 2-3 minutes. The AI solution may also reduce the level of observer variance and increase the number of K17 expressions detected on each slide.

The AI solution may analyze entire tissue sections, flagging areas with potential biomarkers for pathologists to review. Detecting instances of K17 expression typically requires 20× magnification. At this level of magnification, only a relatively small number of cells are visible within the microscopic field of view, requiring more pathologist time to examine and tally all potential K17 expressions in a WSI. The AI solution may highlight specific areas of interest within the WSI. By highlighting the specific areas of interest, the examining pathologist may quickly locate those areas despite the narrow microscopic field of view at the higher magnification levels.

This saves pathologists time and improves consistency in identifying relevant regions. The AI solution may quantify specific features associated with a biomarker, such as the size or intensity of a protein expression. This provides a more objective and standardized assessment compared to traditional visual scoring by pathologists. The AI solution may also analyze complex patterns in pathology images that might be missed by the human eye. This can lead to the identification of new biomarkers relevant for diagnosis, prognosis, or treatment selection.

The reliability and efficacy of AI solutions are impacted by the underlying data they are trained on. Biases in the training data can lead to inaccurate results. Diverse and representative datasets may be used to train AI models that will be used for pathology. Understanding how an AI solution arrives at a conclusion is essential for trust and adoption in clinical settings. For successful implementation, AI solutions should seamlessly integrate into existing pathology laboratory workflows. This may involve developing user-friendly interfaces and ensuring compatibility with other pathology lab systems. Limitations such as limited databases, lack of validation and standardization, systematic errors, and bias prevent AI solutions from seamlessly replacing manual diagnosis in pathology.

Although ML models can offer businesses advantages, such as deep data insights and improved automation, there are technical challenges when building a sustainable and reliable ML model. These challenges may be exacerbated in the context of cytopathology and specifically in the context of detecting threshold levels of cellular K17 expression.

The application of AI and machine learning to cell microscopy requires careful consideration and planning at all stages of the process, including data acquisition, data set curation, selection and deployment of computer-vision methods, and post-deep-learning analysis. If not properly addressed, the challenges associated with each step may limit the scope and reliability of the AI outputs.

For example, ML models may require certain levels of expertise to structure accurately. Training the ML model can be very time intensive. Datasets used to train the ML model may themselves have a higher likelihood of human error, resulting in the ML model learning incorrectly. For example, unlike unsupervised learning models, SML models cannot cluster or classify data on their own.

Furthermore, training an ML model is also difficult because it is hard to optimize the problem presenting, potentially resulting in "underfitting." Underfitting occurs when a ML model is too simple to capture the underlying patterns in the data. It means the ML model hasn't learned enough from the training data, leading to poor performance on both training and test data.

For example, for ML models that utilize a recurrent neural network, underfitting leads to a vanishing gradient problem. During training of the ML model, gradients are used to update the model's weights. For ML models that utilize recurrent neural networks (RNNs), especially deep ones, gradients can become very small as they propagate backward through time. This makes it difficult for the network to learn long-range dependencies in the data.

Saturated units further exacerbate the vanishing gradient problem. When a neuron's input is very large or very small, it becomes "saturated," meaning its output is close to the extreme values of the range. In the saturated regions, the derivative of the activation function (which is used to calculate gradients) is very close to zero. If the RNN's neurons use activation functions that saturate, the already small gradients are effectively "blocked" or reduced to near-zero. The combined effect is that the model fails to learn effectively. The vanishing gradients and saturated units prevent the model from updating its weights properly, leading to poor performance. Both of these problems are likely to occur when training a ML model to detect K17 expressions.

Training a ML model is also difficult due to "overfitting," which results in poor performance in high variance and low bias situations. Overfitting occurs when a ML model learns the training data too well, including its noise and random fluctuations. As a result, the ML model performs exceptionally well on the training data but poorly on new, unseen data (test data). Essentially, the ML model memorizes the training data instead of learning generalizable patterns. Overfitting is common when exploring a space of complex functions and deep nets usually have lots of parameters. Overfitting is also a challenge that may need to be overcome when attempting to train ML models to detect K17 expressions.

To combat these problems with ML models, the following techniques may be utilized:

Different activation functions: ReLU (Rectified Linear Unit) and its variants help mitigate vanishing gradients.

LSTM and architectures: These specialized RNN GRU architectures are designed to address the vanishing gradient problem by incorporating memory cells and gating mechanisms.

Gradient clipping: This technique prevents gradients from becoming too large.

Proper weight initialization: carefully choosing the starting values of the neural network weights.

Batch normalization: A technique that normalizes the activations of each layer, helping to stabilize training. Consideration of these challenges is crucial for building and training effective neural networks, especially in tasks involving sequential data.

Apparatus and methods may include training a ML model to accurately and precisely detect stained urothelial cells that express threshold levels of K17. The ML model would be trained to classify the number of urothelial cells expressing K17 using the following categories: negative or zero (0-4 urothelial cells expressing K17), low expression (less than 5 cells expressing K17), medium expression (5 to 19 cells expressing K17), and high expression (more than 19 cells expressing K17).

An illustrative process for training an ML model to detect K17 expression includes obtaining about 100 unique cases of which 20-30 of them have cells expressing K17 identified on the slide. The identification of K17 expression may be performed by a trained cytopathologist.

An additional set of 100 cases are then submitted to the ML model for detection. The K17 detection results provided by the ML model are then compared to the pathology results generated manually. To reduce over- or underfitting problems, methods may include checking gradients numerically by calculating finite differences. Other techniques for improving ML model performance may include ensuring that the training data includes visualization features that are uncorrelated and have high variance. This may require careful consideration and selection of which slides are presented as training data to the ML model. Features in training data presented to the ML model should be selected to exhibit structure, be uncorrelated and uncorrelated.

Additionally, to improve its diagnostic ability, the ML model be trained iteratively. First, the ML model may be trained on "easy" slides-slides that include readily apparent and clearly visible examples of K17 expression. Depending on concordance of initial ML model results, the ML model may be further refined to account for non-conforming events as well as different levels of K17 expression. This iterative training process may require selecting specialized slides for progressively training the ML model to be capable of detecting less apparent K17 expressions. This process of training and comparing would be repeated until the ML model provides ~98-100% concordance when examining specimens. After achieving this level of accurate detection, more challenging cases would be submitted to the ML model to test against manual pathology results.

An illustrative process for training an ML model to detect K17 expression may include the following steps:

Step #1. Prepare an initial batch of slides which have been marked up to indicate locations of K17 expressions and digitally scanned. Products and services offered by Lumea Inc. of Lehi, Utah such as Viewer+™ may be used to digitize slides. The digitized images may be presented to an ML model with instructions to locate all cells that are DAB (3, 3'-Diaminobenzidine) chromogen stained with at least 2+ intensity. The cells on the initial batch of slides may be marked up so that the ML model can learn which cells are positively expressing a threshold level of K17.

Step #2. After initial review, slides are reviewed cell by cell to make sure the ML model is detecting cells with chromogen staining that positively express K17 and correctly eliminating precipitates and chromogenic deposits (e.g., any other colors, indicators or expressions present on the slide).

Step #3. For each slide, prepare explanations of how the chromogen is binding as well as identifying low levels of cytoplasmic stain. Iteratively train the ML model to identify cells with low, middle and high levels of K17 expression.

Step #4. Design a proof-of-concept AI solution that can identify at least 75-80% of cells expressing K17 that have been identified manually by a trained cytopathologist.

Step #5. Provide the ML model with around 100 unique cases of which 20-30 of them would need to have each cell expressing K17 identified on the slide.

Step #6. Compare ML model classification results to trained pathologist classification results and determine if there is a good level of concordance between both set of results.

Step #7. Provide the ML model with another 100 training slides and compare the ML model classification results to pathologist results for that same set of slides. Refine the ML model to account for non-conforming events. Present the ML model with levels of K17 expression that fall outside the normal (e.g., periphery stain, light colors).

Step #8. Once satisfied with alignment of ML model classification results and trained pathologist classifications (e.g., ~98-100%) concordance, find challenge cases that present difficult K17 expression detection for both the ML model and trained pathologists.

Step #9. If the ML model is able to handle the challenge cases, move ML model into production.

A laboratory diagnostic system for artificial intelligence (AI) identification of urothelial cells exhibiting expression of a Cytokeratin 17 (K17) biomarker is provided. The system may include an AI engine. The AI engine may include one or more ML models. Using the ML mode, the AI engine may be configured to generate an output that identifies a target cell included in a whole slide image (WSI) that expresses a threshold level of K17 expression. The target cell may be a urothelial cell.

The AI engine may be configured to generate an output that identifies each cell that expresses a threshold level of the K17 biomarker in a cluster of cells. An illustrative cluster may include at least two urothelial cells. An illustrative cluster may include at least three urothelial cells. The target cell may be one of a plurality of target cells included in the WSI. The output of the AI engine may identify, in the plurality of target cells, at least one target cell that expresses the threshold level of the K17 biomarker. The output of the AI engine may identify, in the plurality of target cells, at least two target cells that express the threshold level of the K17 biomarker. The output of the AI engine may quantify a level of K17 expression in each of the identified target cells.

The AI engine may be configured to identify a target cell and K17 expression exhibited by the target cell based on specialized training applied to the ML model. The ML model can be trained to consistently analyze cell features such as level of K17 expression, external cell size/shape, and the presence and size of cellular structures. The ML model may be trained to consistently determine how intense the staining should be to classify a cell as positive or negative for K17 expression.

The ML model may be trained to distinguish between a stained cell versus precipitate or other non-cellular material in the WSI. The ML model may be trained to distinguish between urothelial cells and other types of cells in a WSI. For example, the ML model may be trained to determine the minimum size (e.g., in microns) of the smallest benign urothelial cell. The ML model may be trained to reduce the number of false positive cells by disregarding large squamous epithelial cells in a WSI that may express a stain (e.g., DAB).

The ML model may be trained to account for cell size, shape, and whether cells are overlapped in clusters. The ML model may be trained to detect varying degrees of chromogen intensity and the presence of other nearby cells. The ML model may be trained to evaluate other cellular characteristics such as evenness or uniformity of staining, N:C ratio, the presence of other biomarkers, presence of organelles, shape and size of organelles, smoothness of outer cellular edge, and any other suitable characteristics.

The training may include providing, to the ML model, WSIs that exhibit false-positive staining so that the ML model can learn to ignore those instances. The training may include providing the ML model with a distribution of WSIs having staining variations, sample processing and slide preparation variations, and other artifacts to increase the ability of the AI engine to specifically detect target cells expressing threshold levels of K17. The training may include the ML model with a distribution of WSIs acquired by different slide scanners and a distribution of WSIs from multiple laboratories.

The system may include a laboratory information system (LIS). A LIS may function as the "back office" for a laboratory, handling the administrative and operational tasks that support the delivery of diagnostic services. The LIS may be designed to manage all aspects of a laboratory's operations, from specimen tracking and test ordering to results reporting and billing. The LIS may serve as a laboratory's central hub for data management, ensuring accuracy, efficiency, and regulatory compliance.

Specimen tracking may include monitoring location of a specimen throughout the entire testing process, from accessioning to storage. Specimen tracking may also include maintaining a clear chain of custody for the specimen as it is processed and examined by laboratory personnel, instruments or equipment.

The LIS may provide workflow management functions. Such functions may include automating laboratory workflows to streamline processes and reduce errors. Management functions may include the processes and systems involved in connecting laboratory instruments to computers and databases and ensuring the accurate and efficient transfer of data between them. For example, a laboratory may utilize interfaces multiple that allow instruments to communicate with computers or other information systems. Interfaces may include physical connections (e.g., USB, Ethernet, serial ports), software protocols (e.g., file formats, communication standards) and middleware (software that acts as a bridge between different systems). LIS management functions may ensure the interfaces are stable, compatible, and function correctly.

The LIS may provide results reporting functionality. The LIS may generate accurate and timely reports for healthcare providers. The LIS may facilitate electronic data exchange with other systems (e.g., electronic health records). The LIS may also provide quality control functions such as ensuring compliance with regulatory requirements. The LIS may provide billing and financial management functions. The LIS may generate invoices and track financial data.

The LIS may be configured to generate, based on the output generated by the AI engine, a report that quantifies a level of K17 expression in the target cell included in a WSI. The report generated by the LIS may quantify a level of K17 expressed by the plurality of target cells into low grade, medium grade, or high-grade risk of carcinoma, such as urothelial cancer. The low grade may correspond to detection, by the AI engine, of less than 5 target cells in a WSI expressing threshold levels of the K17 biomarker. The medium grade may correspond to 5 to 19 target cells in a WSI expressing threshold levels of the K17 biomarker. The high grade may correspond to more than 19 target cells in a WSI expressing threshold levels of the K17 biomarker. A WSI may include a plurality of cells, such as urothelial cells.

Using conventional diagnostic methods, it takes a highly trained cytopathologist six to ten minutes or even longer to examine a specimen. Other less experienced practitioners may require even more time to examine a specimen. Using the diagnostic system and its AI engine, a diagnostic report may be generated by the LIS within 4-5 minutes after a WSI is presented to a pathologist. The engine may AI allow less experienced practitioners to accurately and efficiently examine the WSI. The report may be generated by the LIS less than 5 minutes after the WSI is presented to the AI engine. In some embodiments, the AI engine may complete analysis of the WSI and present a visual overlay demonstrating notable areas of the WSI in 2 minutes or less after receiving the WSI.

The report generated by the LIS may be associated with a Cohen's kappa score. The Cohen's kappa score may quantify a degree of diagnostic agreement with respect to analysis of a WSI. The Cohen's kappa score may compare observed agreement between two different diagnostic methods while accounting for the possibility that the agreement occurred by chance. Cohen's kappa score produces a value that ranges from −1 to +1. A value of +1 indicates perfect agreement, 0 indicates agreement equivalent to chance and −1 indicates perfect disagreement.

The Cohen's kappa score for the report generated by the LIS may compare consistency of the AI engine's analysis of a WSI to diagnostic assessment of the same WSI by a human pathologist. The report generated by the LIS based on output of the AI engine may be associated with a Cohen's kappa score that is greater than 0.5 with respect to levels of K17 expression detected in a WSI relative to the level of K17 expression in the WSI determined by a human pathologist. The report generated by the LIS based on output of the AI engine may be associated with a Cohen's kappa score that is greater than 0.9 for a level of K17 expression in the WSI, relative to the level of K17 expression determined by a human pathologist.

The diagnostic system may include an image management system (IMS). An IMS may be designed to manage digital pathology images, such as WSIs. The IMS may provide tools for viewing, analyzing, storing, and sharing these WSIs. The IMS may be configured to present WSIs for viewing with an overlay that includes the output generated by the AI engine.

The LIS and IMS may be integrated. For example, the LIS may provide patient and case information to the IMS, ensuring that a WSI is correctly associated with the corresponding slide and case information. The IMS may provide information back to the LIS, such as WSI analysis results or annotations. The LIS may incorporate the information received from the IMS into a clinical report generated for the corresponding patient.

The LIS and IMS may be configured to communicate with each other using an application programing interface (API). Via the API, the IMS may match a WSI to a patient record received from the LIS and link the output of the AI engine to the WSI. Via the API, the LIS may provide access for a cytopathologist to view the WSI of the corresponding patient record and the AI engine output associated with the WSI. The patient record may include case information and metadata associated with the WSI.

Case and slide metadata are important for accurate diagnoses, research, and legal compliance. Case metadata may include patient information (e.g., ID, name, birthdate), clinical information (e.g., diagnosis, type of procedure, specimen collection date, specimen source), and administrative information (e.g., handling instructions, insurance, accession number, date of receipt by laboratory). WSI metadata may include slide identification (e.g., ID, staining method, date of slide preparation), specimen details (e.g., tissue type), digital image information (e.g., scan timestamp, scanner, image resolution, file format, file size) and quality control information (e.g., technician who prepared the slide, staining artifacts).

Apparatus for a LIS is provided. The LIS may include an automated intake pipeline. The automated intake pipeline may link a WSI to metadata associated with the WSI. The metadata may include case metadata and slide metadata. The LIS may include a viewing module. The viewing module may be configured to provide access to view a WSI from within the LIS. The viewing module may be configured to present a toggleable overlay. The toggleable overlay may be toggled on and toggled off. When the overlay is toggled on, it may annotate the WSI and identify a target cell included in the WSI that expresses a target biomarker or other characteristic. When toggled off, the WSI may be presented without any annotations.

The toggleable overlay may be generated by the AI engine. The AI engine may include an ML model that is trained to detect expression of a target biomarker or other cellular characteristic. The target cell may be one of a plurality of target cells. The target biomarker may be K17. The toggleable overlay may identify, in the plurality of target cells, at least two target cells in a WSI that exhibit a threshold level of K17 expression.

The LIS may be configured to generate a pathology report based on the toggleable overlay. The pathology report may flag the WSI as being associated with a low risk for urothelial cancer in response to the AI engine detecting four or less target cells expressing threshold levels of the K17 biomarker. The pathology report may flag the WSI as being associated with a medium risk for urothelial cancer in response to the AI engine detecting 5-19 target cells in the WSI expressing threshold levels of the K17 biomarker. The pathology report may flag the WSI as being associated with a high risk for urothelial cancer in response to the AI engine detecting 20 or more target cells in the WSI expressing threshold levels of the K17 biomarker.

The AI engine may be trained to identify the target cell as expressing the K17 biomarker if it detects that the target cell includes a threshold level of stain intensity in response to exposure to relevant antibodies or other K17 detection methods. In pathology, staining intensity is often graded on a scale of 0 to 3. A "0" represents, negative or no staining. Typically, a 0-level intensity reflects incomplete membrane staining in less than 10% of cells under examination. A "1+" represents weak staining. A "2+" represents moderate staining. A "3+" represents strong staining.

DAB (3,3'-Diaminobenzidine) is a commonly used chromogen in IHC and or ICC processes. When DAB reacts with the enzyme horseradish peroxidase (HRP), it produces a brown precipitate. This precipitate marks the location of the target antigen in a specimen. In an illustrative embodiment, a threshold level of stain intensity may be DAB chromogen staining with at least 2+ intensity.

The AI engine may identify the target cell if it detects that the target cell has a nucleus region that is distinct from a cytoplasmic area and edge of the target cell. Expression of the target biomarker may be detected in the target cell based on a staining intensity of the target cell in response to exposure to the target biomarker. The target cell may be a urothelial cell. The toggleable overlay generated by the AI engine may flag the urothelial cell as exhibiting urothelium duress in response to detecting a threshold level of expression of a target biomarker, such as K17.

An artificial intelligence (AI) method for detecting low-grade urothelial cancer is provided. One of ordinary skill in the art will appreciate that the steps shown and described herein may be performed in other than the recited order and that one or more steps illustrated may be optional. The methods of the above-referenced embodiments may involve the use of any combination of methods, portions of methods, partially executed methods, elements, one or more steps, computer-executable instructions, or computer-readable data structures disclosed herein.

As will be appreciated by one of skill in the art, the invention described herein may be embodied in whole or in part as a method, a data processing system, or a computer program product. Embodiments disclosed herein may be partially or wholly implemented on a computer readable medium, for example, by storing computer-executable instructions or modules or by utilizing computer-readable data structures. Accordingly, the invention may take the form of an entirely hardware embodiment, an entirely software embodiment or an embodiment combining software, hardware and any other suitable approach or apparatus.

Furthermore, such aspects may take the form of a computer program-product stored by one or more computer-readable storage media having computer-readable program code, or instructions, embodied in or on the storage media. Any suitable computer readable storage media may be utilized, including hard disks, CD-ROMs, optical storage devices, magnetic storage devices, and/or any combination thereof.

Software applications may be stored within the non-transitory memory and/or other storage medium. Software applications may provide instructions to the processor circuit that enable components to perform various functions. For example, the non-transitory memory may store software applications such as an operating system, application programs, and an associated database. Some or all of computer executable instructions of the components may be embodied in hardware or firmware. The hardware and firmware may include one or more circuit boards. In some embodiments, the circuit boards may be integrated into a single chip. The chip may be silicon-based.

The AI method may include digitizing a slide carrying urothelial cells. The slide may be digitized using a specialized scanner such as those produced by Hamamatsu Photonics K.K. of Hamamatsu City, Shizuoka Prefecture, Japan. The specialized scanner may be designed to convert traditional glass microscope slides into high-resolution digital images. The scanner may produce extremely detailed digital images, allowing a pathologist or artificial intelligence (AI) engine to examine tissue samples with high accuracy. This digitization process may generate what is known as a whole slide image (WSI). The WSI allows for digital viewing, analysis, and storage of pathology slides.

The AI method may include exposing the WSI to an AI engine. The AI engine may include a trained ML model. The AI engine may quantitate a total number of urothelial cells expressing K17 in the WSI. Based on the total number of urothelial cells and level of K17 expression, the AI method may include scoring the WSI for a threshold risk of urothelial cancer.

The AI method may include using the AI engine to identify at least one urothelial cell on the digitized slide. The AI engine may identify a urothelial cell based on its morphology or other characteristics. The AI engine may generate a visual overlay. Generating the visual overlay may include superimposing one image or graphical element on top of another, creating a composite visual. The visual overlay may be superimposed on a WSI. The visual overlay may have a degree of transparency, allowing the underlying WSI to be seen. This enables the visual overlay to add information, such as annotations without completely obscuring the underlying WSI. The AI engine may ensure accurate positioning and alignment of the visual overlay with respect to the WSI so that target cells within the WSI are accurately annotated or flagged by the visual overlay.

The visual overlay may be used to highlight specific areas of interest in the WSI. For example, the visual overlay may flag or otherwise indicate that at least one of the urothelial cells in the WSI exhibit a threshold risk of urothelial carcinoma. The AI engine may generate the visual overlay based on detecting, within the WSI, one or more urothelial cells that express threshold levels of the K17 biomarker.

Detecting K17 expression typically requires 20× magnification. At this level of magnification, only a relatively small number of cells are visible, requiring more pathologist time to examine and tally all K17 expressions on the slide. The visual overlay may highlight specific areas of interest within the WSI. By highlighting the specific areas of interest, the examining pathologist may quickly locate those areas despite having a small frame of view at the higher magnification levels.

The AI method may include classifying the WSI into low (less than 5 cells expressing threshold levels of K17), medium (5 to 19 cells expressing threshold levels of K17), high (more than 19 cells expressing threshold levels of K17) risk levels for urothelial cancer. The AI methods may include quantifying positively stained urothelial cells in a WSI to aid the diagnosis of urothelial cancer. The output of the AI engine may be presented within a LIS as a visual overlay on top of the WSI.

Current manual identification and scoring systems for detecting K17 expression have limitations in terms of lower accuracy for early detection, medium grade cases, slower turn-around time, and high inter- and intra-observer variability. The AI methods described herein may identify and quantify urothelial cells in a WSI that positively express K17 to aid the reproduceable and consistent diagnosis of urothelial cancer. The AI method may reduce discordance rates associated with examination of WSIs. The AI methods may provide automated, objective, and more consistent, reproducible diagnostic outputs.

An LIS may provide a pathologist access to view a WSI and its associated visual overlay generated by the AI engine. Having access to the WSI directly from within the LIS provides advantages that streamline workflows, improve diagnostic accuracy, enhance collaboration, and ultimately benefit patient care. Instead of switching between separate WSI viewers and the LIS, pathologists can access the digital slide directly from the patient's case within the LIS. This eliminates the need to search for the corresponding image, saving time and reducing the risk of errors associated with manual data entry or misidentification.

With direct and faster access to WSIs from within the LIS, pathologists can review cases more quickly, potentially reducing the overall turnaround time for diagnoses. When accessing the WSI from within the LIS, the WSI is displayed alongside relevant patient demographics, clinical history, prior reports, and other lab results already stored in the LIS. This provides a comprehensive view of the case, aiding in more informed diagnostic decisions. Additionally, direct WSI access from within the LIS allows pathologists to link specific areas of interest on the WSI directly to their findings and interpretations within the LIS report, creating a more integrated and visually informative report.

Linking the WSI directly to the LIS record helps ensure that the correct digital image is associated with the correct patient and case, minimizing the risk of diagnostic errors due to slide mix-ups. The LIS may allow multiple pathologists to view and annotate the same WSI simultaneously, enabling real-time discussions and collaborative diagnostic decision-making, especially for complex or challenging cases. Having access to WSIs directly from within the LIS creates a more efficient, accurate, collaborative, and ultimately safer environment for pathology practice. Such integration into the existing laboratory workflow leads to improved patient care, lower healthcare costs and better clinical outcomes.

The pathologist may review the WSI and annotations provided by the visual overlay to quantify positively stained urothelial cells in the WSI. The AI methods may include calculating Cohen's kappa between the levels of K17 expression in pathologist's report regarding the WSI and the AI engine's analysis regarding the WSI.

The AI methods may include recursively training one or more ML models that are used by the AI engine to detect and quantify urothelial cells that express the K17 biomarker. The ML model may be recursively trained based on detecting differences between a visual overlay generated for a WSI and a diagnosis provided for the same WSI authored by a pathologist. For example, clusters of urothelial cells with random levels of K17 expression are typically a challenge for ML models to accurately detect and identify. However, with recursive training, the ML model may improve its recognition of individual cells within such clusters. Additionally, even using the AI model to flag the cluster itself is a valuable diagnostic tool. Flagging the cluster, such as by annotating or flagging it in the visual overlay, makes the pathologist aware that the cluster should be closely examined for individual cells within the cluster that may be expressing threshold levels of K17.

A WSI may include numerous cells with varying degrees of K17 expression. In some cases, there will be sufficient K17 expression among the numerous cells for the AI engine to classify the WSI as a positive indicator of urothelial duress. However, in many instances the cluster of cells with varying degrees of expression may be the only cells in a WSI that are K17 positive. For example, a WSI may include a papillary cluster which itself is a structure that raises suspicion and warrants further investigation. A papillary cluster may be an arrangement of cells that resembles finger-like or frond-like projections.

In some cases, a cluster, as a whole, may not express a threshold level of the K17 biomarker. However, individual cells within the papillary cluster may express the threshold level of K17. The AI engine may detect and classify the individual, positive expressing cells within the cluster. At a minimum, the AI engine may generate a visual overlay that flags the cluster to a pathologist. This is an especially valuable diagnostic tool in lower expressing WSIs, where it is important that individual cells, which may on their own exceed a threshold level of K17 expression, be brought to the attention of the pathologist.

Apparatus may include a ML model that is configured to detect levels of K17 expression in a voided urine sample. The ML model may be a supervised ML model. The voided urine sample may include one or more urothelial cells. The voided urine sample may include benign bladder mucosa, urothelial cells or transitional epithelial cells. The voided urine sample may be converted into a whole slide image.

The ML model may be configured to detect K17 expression in the urine sample or WSI in less than 5 minutes. In some embodiments the time savings may be more than 50% compared to conventional techniques. In addition to yielding more accurate and consistent analysis/diagnoses. The ML model may be configured to achieve a concordance level of at least 90% across variations in staining intensity, slide preparation techniques and volume of cells in WSI.

A method for training a ML model to detect levels of K17 expression in a voided urine sample is provided. The method may include presenting an initial cohort of cells expressing K17 expression to the ML model. The method for training may include using the ML model to locate cells within the WSI that are DAB (3, 3'-Diaminobenzidine) chromogen stained and exhibit at least 2+ intensity. The method may include training the ML model to differentiate between cells that exhibit K17 chromogen staining and other chromogenic deposits. The method may include further training the ML model to detect cells exhibiting low, middle and high levels of K17 expression. The method may include further training the ML model to detect cells exhibiting any suitable characteristics, such as N:C ratio, presence of a nucleus, shape or unique features.

The method may include training the ML model to correctly identify 75-80% of the cells having K17 expressions that have been identified by a trained pathologist. The method may include training the ML model by presenting at least 100 unique WSIs of which 20-30 of them each have at least one cell expressing a threshold level of K17. The method may include training the ML model using a second set of 100 WSIs. The method may include training the ML model using the second set of 100 WSIs to identify levels of non-conforming (e.g., negative) K17 expression. The method may include training the ML model to achieve ~98-100% concordance of K17 expression detection with detection levels identified by a trained pathologist.

Apparatus and methods in accordance with this disclosure will now be described in connection with the figures, which form a part hereof. The figures show illustrative features of apparatus and method steps in accordance with the principles of this disclosure. It is to be understood that other embodiments may be utilized, and that structural, functional and procedural modifications may be made without departing from the scope and spirit of the present disclosure.

The steps of methods may be performed in an order other than the order shown and/or described herein. Method embodiments may omit steps shown and/or described in connection with illustrative methods. Method embodiments may include steps that are neither shown nor described in connection with illustrative methods. Illustrative method steps may be combined. For example, an illustrative method may include steps shown in connection with any other illustrative method and/or apparatus.

Apparatus may omit features shown and/or described in connection with illustrative apparatus. Apparatus embodiments may include features that are neither shown nor described in connection with illustrative apparatus. Features of illustrative apparatus may be combined. For example, an illustrative apparatus embodiment may include features shown or described in connection with any other illustrative apparatus and/or method embodiment.

FIG. 1 shows an illustrative table demonstrating the efficacy of the Acu-URO17 test for early detection of potential UC based on expression of K17. FIG. 1 shows a table that compares results of a standard cytology with results of the Acu-URO17 test.

The "CYTOLOGY" column describes the diagnosis of the urine cytology resulting from Acu-URO17 testing. The cytology results range from definitively cancerous to negative for malignancy. The categories (rows) in the CYTOLOGY column include:

CANCER: Specimens that include clearly malignant urothelial cells.

SUSPICIOUS: Specimens that include urothelial cells that are potentially malignant or associated with malignancy, but not definitively so.

ATYPICAL: Specimens that include urothelial cells that show some abnormalities but are not clearly malignant or suspicious.

NEGATIVE: Samples with urothelial cells that appear normal.

The "N" column shows the total number of urine samples or specimens, for each row in the CYTOLOGY column. The "URO17 EXPRESSION (TOTAL)" column shows the total number of specimens in each row of the CYTOLOGY column that showed any level of K17 expression (either high or low). It also shows the percentage of specimens in each row that exhibited K17 expression.

The "URO17 HIGH EXPRESSION" column shows the number of specimens in each category that showed high levels of K17 expression, along with the percentage of samples in that category that showed high expression. The "URO17 LOW EXPRESSION" column shows the number of specimens in each category that showed low levels of K17 expression, along with the percentage of samples in that category that showed low expression. The "URO17 NEGATIVE" column shows the number of specimens in each category that showed no detectable K17 expression, along with the percentage of samples in that category that were negative for K17.

The data shown in FIG. 1 shows that K17 expression, particularly high levels of expression, is associated with UC malignancy. All cancer samples showed K17 expression, and a high percentage of suspicious and atypical samples also showed K17 expression. A significant portion (88%) of samples with negative cytology showed no K17 expression, suggesting that K17 may have reasonable specificity (i.e., it's not often positive when cancer is truly absent). It's important to note that K17 expression was also observed in some samples with suspicious, atypical, and even negative cytology. This may mean that K17 is not a perfect marker and may not be able to definitively diagnose cancer on its own.

The varying levels of K17 expression (high vs. low) in different cytology categories might be useful for risk stratification. For example, a patient with atypical cytology and high K17 expression might be considered at higher risk for UC than a patient with atypical cytology and low K17 expression. In summary, the table shown in FIG. 1 provides evidence that K17 expression, especially high expression, is associated with the presence of cancer or pre-cancerous conditions in urine samples.

FIG. 2 shows results of a study examining the expression of the K17 biomarker in urine samples, categorized by cytology findings and further stratified by FISH (Fluorescence In Situ Hybridization) testing results. FIG. 2 confirms that Acu-URO17 is a clinically relevant, non-invasive, and cost-effective tool to be used in conjunction with both urine cytology and FISH testing in the diagnosis and management of UC. Acu-URO17 is more cost-effective because it is non-invasive and may lead to an early diagnosis that allows physicians to spend time examining other patients. Acu-URO17 also allows for repeat testing without discomfort to the patient, less risk of infection and at a lower cost.

The "CYTOLOGY" column in FIG. 2 describes the interpretation of the urine cytology, ranging from definitively cancerous to negative for malignancy. The row or categories in the CYTOLOGY column include:

CANCER: Samples with urothelial cells that are clearly malignant.

SUSPICIOUS: Samples with urothelial cells that are potentially malignant, but not definitively so.

ATYPICAL: Samples with urothelial cells that show some abnormalities but are not clearly malignant or suspicious.

NEGATIVE: Samples with urothelial cells that appear normal.

The "N" column represents the total number of urine samples in each cytology category. The "URO17 EXPRESSION (TOTAL: H+L)" column shows the total number of samples in each cytology category that showed any level of K17 expression (either high or low), along with the percentage of samples in that category that exhibited K17 expression. It is further broken down by FISH results (positive or negative).

The "URO17 HIGH EXPRESSION" column shows the number of samples in each category that showed high levels of K17 expression, along with the percentage of samples in that category that showed high expression. It is also broken down by FISH results. The "URO17 LOW EXPRESSION" column shows the number of samples in each category that showed low levels of K17 expression, along with the percentage of samples in that category that showed low expression. It is also broken down by FISH results.

The "URO17 NEGATIVE" column shows the number of samples in each category that showed no detectable K17 expression, along with the percentage of samples in that category that were negative for K17. It is also broken down by FISH results.

The data in FIG. 2 suggests that K17 expression, particularly high expression, is associated with malignancy. All cancer samples showed K17 expression, and a high percentage of suspicious and atypical samples also showed threshold levels of K17 expression. A significant portion (67%) of samples with negative cytology also showed no K17 expression, suggesting that K17 may have reasonable specificity (i.e., it's not often positive when cancer is truly absent). It's important to note that K17 expression was also observed in some samples with suspicious, atypical, and even negative cytology. This means that K17 is not a perfect marker and may not be able to definitively diagnose cancer on its own.

The data in FIG. 2 is further stratified by FISH results (positive or negative). FISH is a technique used to detect specific genetic abnormalities associated with cancer. FIG. 2 provides an analysis of the relationship between K17 expression, cytology, and genetic markers. The varying levels of K17 expression (high vs. low) in different cytology categories, combined with FISH results, might be useful for risk stratification.

For example, a patient with atypical cytology, high K17 expression, and a positive FISH result might be considered at higher risk for cancer than a patient with atypical cytology, low K17 expression, and a negative FISH result. This presents data that could be helpful in lowering the likelihood that a patient may be asked to undergo a more expensive, invasive cystoscopy procedure.

In summary, the data in FIGS. 1 and 2 provide evidence that K17 expression, especially high expression, is associated with the presence of cancer or pre-cancerous conditions in urine samples. The addition of FISH results may provide further insight into the relationship between K17 expression, cytology, and genetic abnormalities. It's important to note that K17 expression testing or FISH results are not perfect tests and should be interpreted in conjunction with other clinical and pathological findings. However, testing for K17 expression may lead a physician to consider a less invasive approach or closer monitoring instead of immediate cystoscopy, especially if the patient has no other concerning symptoms.

FIG. 3 shows three panels of microscopic images of stained cells. Each panel displays a collection of individual cells. The cells exhibit varying shapes and sizes, which is typical in biological samples. The cells are stained with a brown chromogen, indicating the expression of the K17 biomarker, which allows for the visualization of K17 expression within the cells. In some cells, a blue stain is visible, which is likely a counterstain (such as hematoxylin) used to visualize the cell nucleus.

In FIG. 3, the Left Panel shows a mix of round and irregular-shaped cells. The brown staining is relatively uniform and intense in most cells with minimal to no visible nuclear counterstain, suggesting high expression of the target protein. In the Middle Panel, cells are generally more uniform in shape, mostly oval or slightly elongated. The brown staining is also relatively uniform and less intense. Blue nuclei are also visible in this panel. The Right Panel shows a wider variety of cell shapes, including some with irregular extensions. The brown staining intensity varies across cells, with some showing stronger staining than others. Blue nuclei are visible.

An ML model may be trained based on the microscopic images shown in FIG. 3. For example, based on training the ML model using images shown in FIG. 3, an AI engine may be configured to detect cells that positively express K17. For example, based on the data in FIG. 3, the ML model may be trained to identify a cell as positive for K17 expression if it exhibits light to high staining, with a clearly visible nucleus or distinguishable nuclear material. Additionally, the training images teach the ML model that positively expressing cells will likely have a nucleus region that is distinct from the cytoplasmic area and the cell edge. Based on the data in FIG. 3, the ML model may be trained such that a cell which is lightly-stained but has visible blue nucleus or even representation of nuclear material which is different from cytoplasm/cell edge should be classified as positive for K17 expression.

FIG. 4A shows images that may be used to train an ML model to detect cells that positively express the K17 biomarker. The cells shown in FIG. 4A are generally consistent in shape, being round to slightly oval. The brown staining intensity varies somewhat between cells and some cells appear more intensely stained than others. However, generally, all the cells shown in FIG. 4A may be considered to have a high staining intensity and are considered to exceed a threshold level of K17 expression.

The cells shown in FIG. 4A also include a visible nucleus or cellular material. In some of the cells, a faint, darker area within the cell represents the nucleus or cellular material. The cells shown in FIG. 4A appear to be relatively uniform in size, helpful for teaching the ML model to identify a target cell based on size. Based on the information shown in FIG. 4A, the ML model can be trained to analyze a WSI and determine a level of K17 expression, external size/shape, and the presence and size of cellular structures.

Figure 4B:
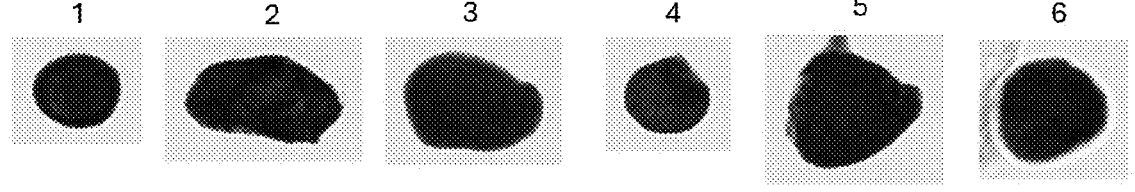
FIG. 4B shows illustrative microscopic images.

FIG. 4B shows images that may be used to train an ML model to detect cells that positively express the K17 biomarker. Cell #1 is a round cell with relatively uniform brown staining. Cell #2 is a larger, irregularly shaped cell with a more intense and uneven brown staining. Cell #3 is a rounded cell with a slightly less intense and more uniform brown staining compared to Cell #2. Cell #4 is a smaller, more elongated cell with less intense brown staining. Cell #5 is a larger, irregularly shaped cell with a dark, intense brown staining, particularly at one end. Cell #6 is a round cell with a fairly uniform brown staining.

The cells shown in FIG. 4B exhibit high intensity staining. However, the high intensity staining makes it challenging to confirm whether a nucleus is present. The ML model may be trained to identify cells similar to those shown in FIG. 4B as positives due to their circular shape and high staining intensity without any folds or wrinkles in their membrane. The absence of folds suggests that the cells are likely not undergoing significant changes in shape or volume, which could occur during processes like apoptosis (programmed cell death) or mechanical damage. It also suggests that the cells are relatively intact and not artifactually distorted during processing.

Figure 4C:
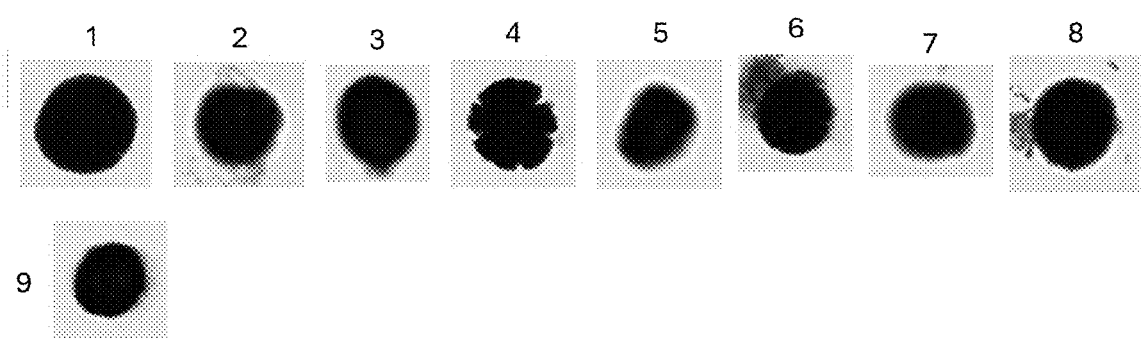
FIG. 4C shows illustrative microscopic images.

FIG. 4C shows images that may be used to train an ML model to detect cells that positively express the K17 biomarker. Cell #1 is a round cell with relatively intense and uniform brown staining. Cell #2 is an oval cell with slightly less uniform staining. Cell #3 is a round cell with a dark, intense brown staining. Cell #4 is a clumped or aggregated cell with very dark staining, potentially representing multiple cells or debris. Cell #5 is an oval cell with intense and uniform staining. Cell #6 is a cell with a visible background blue/purple stain (likely a counterstain) in addition to the brown staining. Cell #7 is a round cell with a darker, intense brown staining. Cell #8 shows dark staining and additional artifacts. Cell #9 (bottom) is a round cell with relatively uniform dark brown staining.

The cells in FIG. 4C exhibit an intense brown and nearly black staining which may indicate a cell with very high expression levels of K17 or possibly a non-cellular precipitate. Because of the intensity of the staining, for all the images in FIG. 4C, there is little to no visible internal detail such as nuclei or subcellular structures. While the stain color is nearly black, it is not entirely black like typical precipitates. Additionally, precipitates generally have more irregular shape and size. The ML model may be trained to identify the cells shown in FIG. 4C as cells positively expressing K17.

Figure 5A:
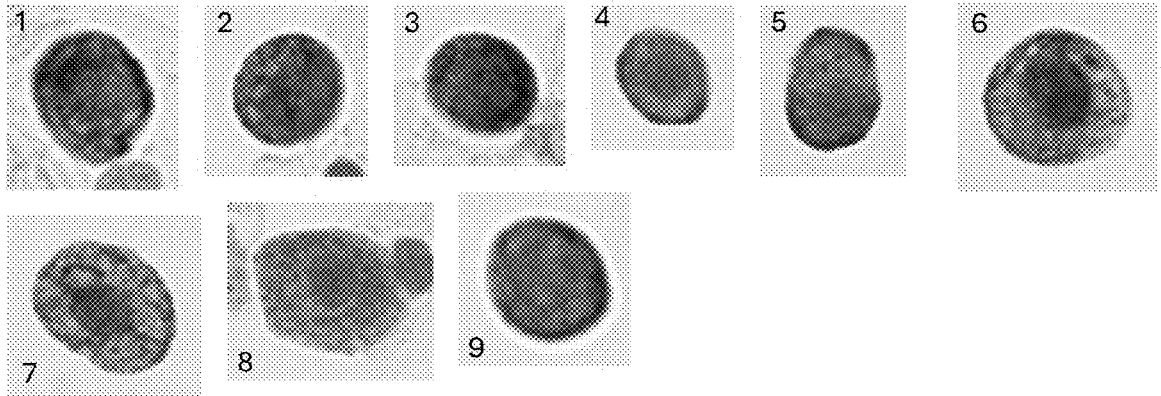
FIG. 5A shows illustrative microscopic images.

FIG. 5A shows images that may be used to train an ML model to detect cells that positively express the K17 biomarker. The cells in FIG. 5A show brown staining in the cytoplasm and clearly visible blue nuclei, indicating that the staining intensity is moderate to low, allowing cellular detail to be seen.

Cell #1 is a round cell with a uniform light brown staining and a visible blue nucleus. Cell #2 is a round cell with a slightly less intense brown staining and a visible blue nucleus. Cell #3 is a round cell with a visible blue nucleus and brown staining. Cell #4 is a round cell with a well-defined blue nucleus and less intense brown staining. Cell #5 is an oval cell with a visible blue nucleus and a relatively uniform brown staining. Cell #6 is a round cell with a distinct blue nucleus and brown staining. Cell #7 is an oval shaped cell with a visible blue nucleus and less intense brown staining. Cell #8 is a round cell with a distinct blue nucleus and a less intense, more granular brown staining. Cell #9 is a round shaped cell with a visible nucleus and uniform brown staining.

The cells shown in FIG. 5A are classified as positively expressing K17 due to their relatively strong brown staining and clearly visible nucleus. Unlike negatives, which typically show uneven, blushing-like staining, the cells shown in FIG. 5A exhibit nearly uniform staining and well-defined perimeters. The cells shown in FIG. 5A exhibit a stain intensity of about 2+ that is at or just over a threshold level for positively expressing K17.

Figure 5B:
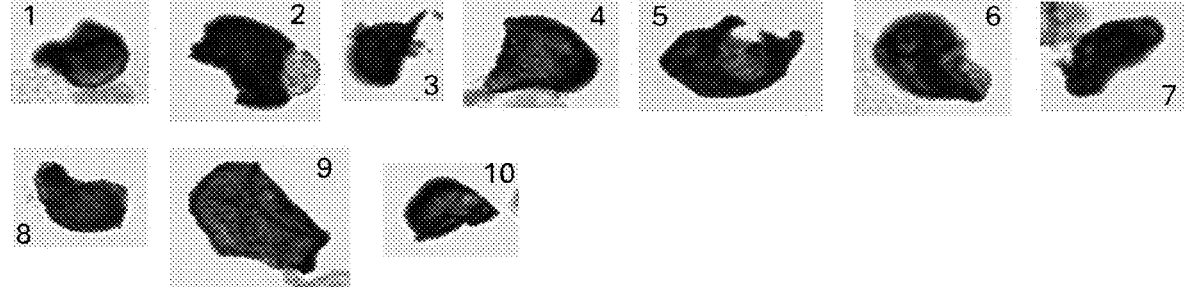
FIG. 5B shows illustrative microscopic images.

FIG. 5B shows cells that may be used to train an ML model to detect cells that should be flagged for further review by a pathologist. The cells in FIG. 5B have irregular shapes and are less round compared to those in FIGS. 4A-5A, possibly indicating they are a different cell type or in a state of cell activation, migration, or morphological change (e.g., due to treatment or stress). The cells in FIG. 5B have visible nuclei, however, they show less blue/purple counterstain visible, possibly suggesting the nuclei are not clearly stained, the intense brown staining is masking nuclear detail, or they are not urothelial cells. Some cells in FIG. 5B show heterogeneous staining, with darker and lighter regions, indicating variable antigen distribution or partial staining.

In FIG. 5B, cell #1 is irregularly shaped with a dark brown staining and a small area of blue staining (likely counterstain). Cell #2 is an irregularly shaped cell with a dark brown staining and a folded appearance. Cell #3 is a small, irregularly shaped cell with a dark brown staining. Cell #4 is an irregularly shaped cell with a dark brown staining and a distinct fold. Cell #5 is an irregularly shaped cell with a dark brown staining and a somewhat clumped appearance. Cell #6 is an irregularly shaped cell with a dark brown staining and a more elongated shape. Cell #7 is an irregularly shaped cell with a dark brown staining and a more compact shape. Cell #8 is an irregularly shaped cell with a dark brown staining and a folded appearance. Cell #9 is an irregularly shaped larger cell with a dark brown staining and a more elongated shape. Cell #10 is a small, irregularly shaped cell with a dark brown staining and a fragmented appearance.

Cells relatively larger to others in voided urine and that are rounded and smooth are the hall mark of UC that can be detected in voided urine. The cytopathologist typically looks for cells that have a threshold nuclear to cytoplasmic ratios (N:C). The nuclear-to-cytoplasmic (N:C) ratio is a valuable morphologic feature for the diagnosis of atypia and malignancy in the cells present in voided urine. Typically, the presence of high N:C ratio cells in a cellular population that normally displays a low to moderate N:C ratio is a sign of cellular atypia and even malignancy.

When the N:C ratio is just at the threshold or a little larger (illustrative cut off is ~>0.5), cells that are at or slightly above this threshold may only be classified by the cytopathologist as atypical. However, when also considering the K17 expression of these borderline cells helps the pathologist determine if the atypia they are identifying is likely to progress to UC in the absence of any of the previously mentioned cause for atypia. Borderline cells that positively express K17 are more likely to progress to UC malignancy.

Each of the cells shown in FIG. 5B, although irregularly shaped, exhibit high staining and a visible nucleus. Additionally, their size is smaller than that of larger squamous epithelial cells, which can be found in voided urine. The ML model may be trained to identify cells of the type shown in FIG. 5B, and the AI engine may flag them to a pathologist in a visual overlay presented via a LIS.

Figure 5C:
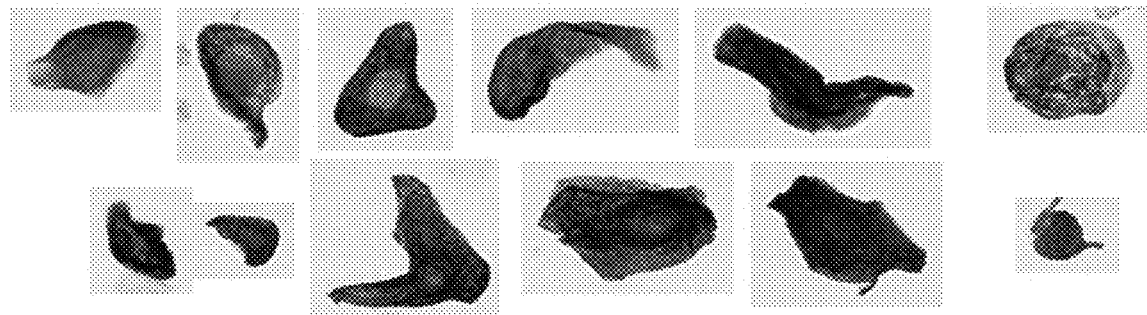
FIG. 5C shows illustrative microscopic images.

FIG. 5C shows cells that may be used to train an ML model to detect cells that should be flagged for further review by a pathologist. FIG. 5C shows irregularly shaped cells with some showing extensions, folds, and variations in thickness. The cells shown in FIG. 5C also exhibit high staining and a visible nucleus. However, the cells shown in FIG. 5C generally exhibit less staining intensity compared to the cells shown in FIG. 5B.

Each of the cells shown in FIG. 5C, although irregularly shaped, exhibit high staining and a visible nucleus. Additionally, their size is smaller than that of larger squamous epithelial cells, which can be found in voided urine. The ML model may be trained to identify cells of the type shown in FIG. 5C, and the AI engine may flag them to a pathologist for further investigation. The cells may be flagged in a visual overlay generated by the AI engine and presented to the pathologist within a LIS or IMS.

Figure 6A:
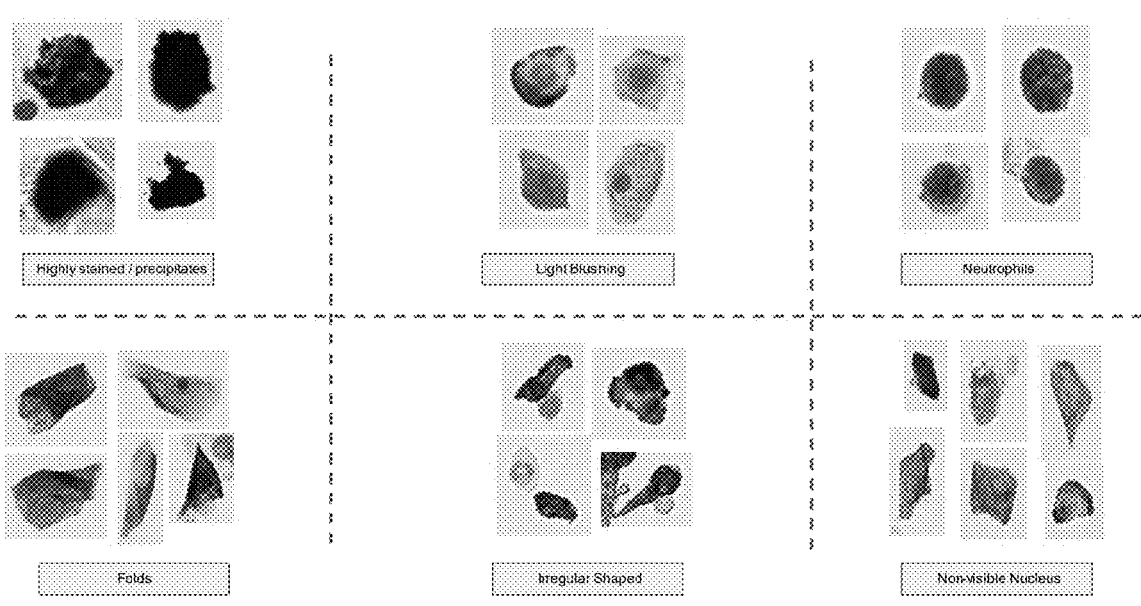
FIG. 6A shows illustrative microscopic images.

FIG. 6A shows a compilation of categorized microscopic images highlighting different staining and morphological characteristics. The cell images shown in FIG. 6A may be used to train an ML model to recognize cells that are negative for or express less than a threshold level of K17. Generally, the images shown in FIG. 6A are classified as negative for K17 expression because they may include folds that display uneven staining along the edges, are neutrophils that are small in size and exhibit two nuclei or even if high/light stained, have no distinct nucleus.

The images in FIG. 6A labeled "Highly Stained/Precipitates (top left) contains images of dark, irregularly shaped masses. These appear to be clumps of material or cells with very intense staining, possibly due to an accumulation of the stain or precipitates. The structure of individual cells is difficult to discern. These images are likely precipitates. Images in FIG. 6A labeled "Light Blushing" (top middle) shows cells with a faint, diffuse staining pattern. The cells are generally intact and show internal structure, including visible nuclei. The staining intensity is generally under a threshold level for positive K17 expression.

Images in FIG. 6A that are labeled "Neutrophils" (top right) show cells with the characteristic morphology of neutrophils, a type of white blood cell. These cells have multi-lobed nuclei and a relatively uniform staining pattern. These are likely immune cells, not the target epithelial cells relevant for UC detection. The images in FIG. 6A labeled "Folds" (bottom left) contains images of cells with prominent folds or wrinkles in their membranes. These folds can trap stain unevenly, leading to misleading patterns. The presence of folds suggests that these have undergone shrinkage or distortion during cells may preparation. The staining pattern is variable.

The images in FIG. 6A labeled "Irregular Shaped" (bottom middle) show cells with a variety of unusual or asymmetrical shapes. These cells deviate from the typical round or oval morphology that typically characterizes urothelial cellular atypia and or malignancy. The staining pattern and nuclear visibility vary.

The images in FIG. 6A labeled "Non-visible Nucleus" (bottom right) show cells where the nucleus is not clearly visible, despite light staining intensity. The staining pattern is relatively uniform, but the internal structure of the cells is not well-defined. The cells are also irregularly shaped.

The ML model may be trained to identify cells or structures of the type shown in FIG. 6A. In some embodiments, the AI engine may identify the cells or structures of FIG. 6A to a pathologist as negative for K17 expression. The AI engine may label the cells or structures as negative for K17 expression in a visual overlay presented to the pathologist. In other embodiments, the AI engine may not annotate or flag the cells and structures shown in FIG. 6A in a visual overlay. In those embodiments, the visual overlay may be configured to only flag cells that are positive or require further review by the pathologist.

In other embodiments, the AI engine may generate two or more visual overlays. A first visual overlay may flag cells identified by the ML model as being negative for K17 expression or any other biomarker. A second visual overlay may flag cells that are identified by the ML model as being positive for K17 expression or any other biomarker. A third visual overlay may flag cells that are identified by the ML model as needing further review by the pathologist. A pathologist may toggle between the different visual overlays and display one or more of them, or none of them, when examining a WSI.

Figure 6B:
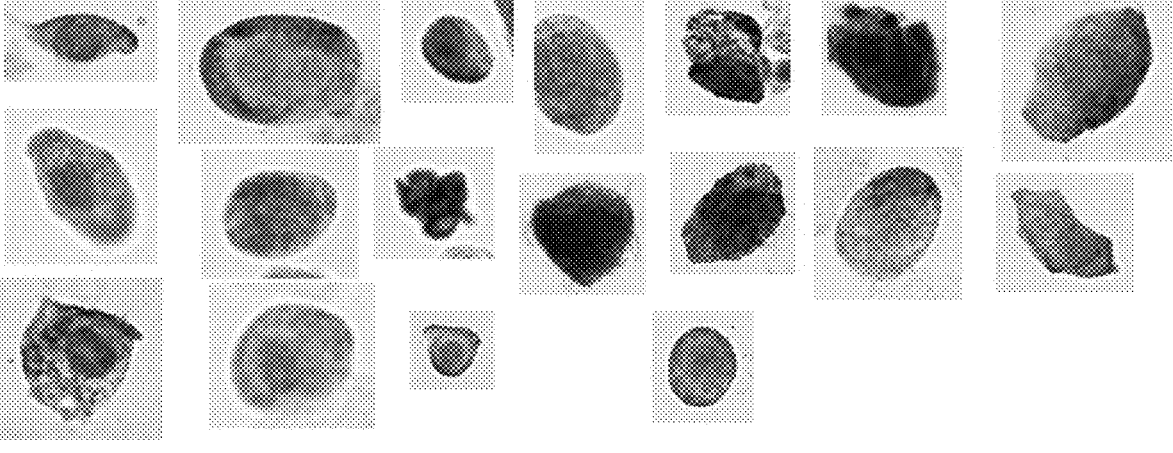
FIG. 6B shows illustrative microscopic images.

FIG. 6B shows images that may be used to train an ML model to identify cells that are negative for K17 expression. The images shown in FIG. 6B are "negative" due to factors including light staining, uneven perimeter staining, irregular shapes, or the absence of a visible nucleus.

FIG. 7A shows how ongoing training of an ML model has improved the AI engine's ability to distinguish between negative samples and non-cellular noise. For example, a prior version of the ML model may have been incorrectly identifying objects shown in the "Negative Samples" panel as negative. In the context of detection for K17 expression, a negative identification presupposes that the objects identified are in fact urothelial cells. Alternatively, the prior version of the ML model may have been identifying the objects shown in the "Negative Samples" as positively expressing K17. Generally, it may be undesirable for the ML model to detect non-cellular precipitates when there is no cellular material present.

Upon further training of the ML model, in an updated version, the objects shown in the "Negative Samples" panel are no longer being classified as negative or positive. With additional training, the ML model now correctly determines that the browns and material in the "Negative Samples" panel are chromogen precipitates and are not cells.

The improved ML model is less susceptible to false positives and includes improved noise filtering. The positive samples, which are consistently identified by both versions, likely represent the true positive detections. The AI engine has been improved to reduce the amount of noise or false positives in its classification. As a result of this improvement, the AI engine is expected to be more accurate in distinguishing between negative and positive samples, leading to more reliable cell counting or classification results.

FIG. 7A shows that further training of the ML model did not impact the detection of cells that do positively express K17. The cell shown in the "Positive Samples" panel were flagged by the ML model as being positive for K17 expression in both versions of the ML model.

FIG. 7A also shows green and purple bounding boxes annotating or flagging target areas. The bounding boxes may be added by an AI engine in response to detection by the ML model. The bounding boxes may be included in a visual overlay generated by the AI engine.

FIG. 7B shows how the ML model may use area thresholds to filter objects in a WSI that are too large or too small to be considered a target (e.g., urothelial) cell. In the context of evaluating for K17 expression, a chromogen (DAB) is typically used to stain the positive cells. The immunohistochemistry (IHC) or immunocytochemistry process (ICC) typically leaves artifact staining on the slide and in the resulting WSI.

To help facilitate accurate detection of the positive stained urothelial cells (and not other types of cells), the ML model may also be trained to determine the minimum size (e.g., in microns) of the smallest benign urothelial cell. In addition, the ML model may be trained to identify large squamous epithelial cells that may pick up the DAB stain. The ML model may be trained to discard or ignore the squamous epithelial cells to reduce the number of false positive urothelial cells detected by the ML model. Illustrative training parameters for area thresholds may be:

Lower threshold: $700$ pixel$^2$~$(26.45$ pixel$)^2$~$(5.8$ $\mu$m$)^2$

Upper threshold: $14000$ pixel$^2$~$(118.32$ pixel$)^2$~$(26.03$ $\mu$m$)^2$

FIG. 7B shows two examples (cell #1 and cell #2) of highly stained (brown coloration) epithelial cells which were detected by the ML model but rejected due to exceeding the upper area thresholds. The highly stained epithelial cells, despite being detected and exhibiting a high stain intensity, were deemed by the ML model to be too large and therefore excluded from further analysis in connection with target urothelial cells.

As a further example, the ML model may be iteratively trained. Initially, the ML model may be trained to classify objects in a WSI as either HC (high confidence) or as LC (low confidence). Objects in the WSI that are highly likely to be urothelial cells exhibiting a threshold level of K17 expression may be flagged as HC. Objects that may be a urothelial cell and may have some characteristics atypical for benign urothelial cells may be flagged at LC. LC objects may be flagged by the ML model for further review by a pathologist.

Over time, with additional exposure to different objects, annotations and additional WSIs, the ML model continuously improves its diagnostic ability and evolves to only identify urothelial cells that express a threshold level of K17. For example, the ML model may learn to set a lower area threshold that rejects small, intensely stained objects, while preserving the detection of larger, legitimate urothelial cells. Likewise, the ML model may reject very large epithelial cells.

Figure 8A:
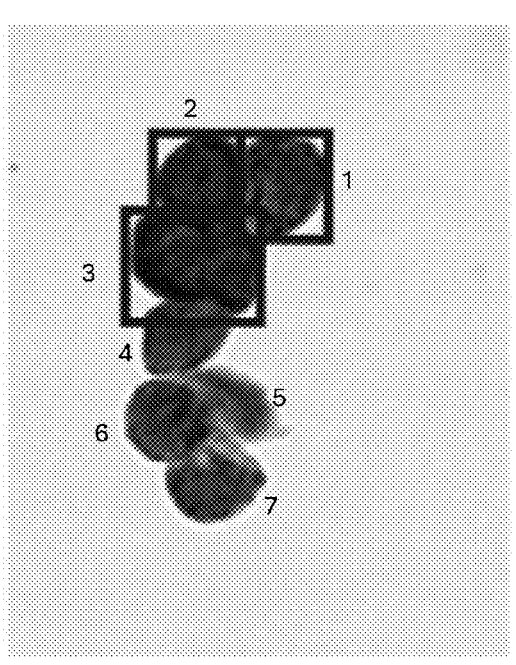
FIG. 8A shows an illustrative microscopic image.

FIG. 8A shows an illustrative ML model's progressive performance in identifying cells in a WSI that includes a cluster of cells. Within a cluster, different cells may have different levels of K17 expression. It may also be challenging for the ML model to definitively identify individual cells in the cluster. Accordingly, clusters are challenging for the ML model to detect, identify and diagnose. Ideally, the ML model should determine that there are 7 individual cells in the cluster shown in FIG. 8A.

The blue bounding boxes in FIG. 8A show that an initial version of the ML model has identified the top three cells in the cluster. The three lower cells shown in FIG. 8A have incomplete circumferential membranous staining with lighter brown staining. This lighter level of staining is hard for the ML model to assess, because it is unclear whether the cells are not expressing K17 or whether the cluster not lying flat to the slide when the WSI was generated. Initially, ML model may be trained to only identify the top three cells of the cluster as positively expressing K17. The ML model may flag the cluster to a pathologist for further examination and identification of additional cells.

However, the ML model may be improved by further training such that the ML model locates and identifies four additional (lower) cells in FIG. 8A. With subsequent training, the ML model may successfully identify the cluster as including seven cells and flag the cluster (e.g., in visual overlay generated by the AI engine) to a pathologist for further examination.

In some embodiments, the ML engine may be configured to isolate each cell in a cluster and the AI engine may be capable of presenting an individual cell part of cluster together with other cells in the cluster. Such a group presentation may provide helpful context to the examining pathologist. In some embodiments, the ML engine may be configured to isolate each individual cell in a cluster and the AI engine may be capable of presenting each individual cell independently.

For example, in the context of FIG. 8A, the ML model may isolate cell #3 from the cluster. The AI engine may then be capable of displaying cell #3 independently of the remaining cells in the cluster. Thus, the AI engine may present cell #3 so that it can be examined without any other nearby cells (e.g., cell #s 1, 2 or 4) and so that it can be examined without any contextual influence of the nearby cells. The ability to isolate a cell in a cluster and present it independently may allow that isolated cell to be more accurately assessed for levels of K17, shape or any other characteristics. The AI engine may present one or more isolated cells in separate visual overlays.

Figure 8B:
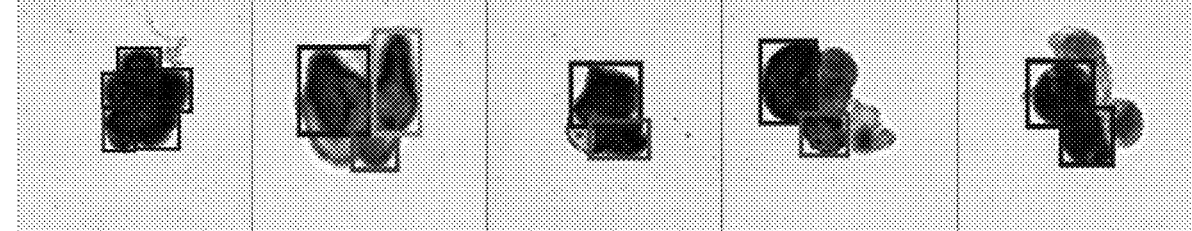
FIG. 8B shows illustrative microscopic images.

In FIG. 8B shows an illustrative visual overlay in which the ML model has successfully labeled identified cells in a WSI with bounding boxes, showing robust automated cell detection and classification by the ML model. FIG. 8B shows the ML model's ability to identify clusters, count target cells in the cluster and differentiate, based on staining intensities and other factors, between high confidence (HC) and low confidence (LC) levels of K17 expressing cells within the cluster.

The red and blue bounding boxes shown in FIG. 8B identify HC cells. The blue bounding boxes specifically identifies the ML model's top HC cells (e.g., top 20 HC cells), based on the ML model's confidence scoring schema. The green bounding box shown in FIG. 8B identifies LC cells. Cells or other objects that are not enclosed by bounding boxes either express less than a threshold level of K17 or have been determined not to be a target cell.

Cells identified and enclosed within a bounding box may be presented independently and alone, without including any other neighboring cells. The ability to isolate cells in a group or cluster and present each of them independently may allow those cells to be more accurately assessed for levels of K17, shape or any other characteristics. The AI engine may present one or more isolated cells in a separate visual overlay.

When generating a WSI, a slide may occasionally be scanned slightly out of focus. Generally, a pathologist may request a rescan in response to encountering an out-of-focus WSI. FIG. 9 shows that despite an underlying slide having been scanned out-of-focus, the ML model may still successfully identify target cells in the resulting WSI as positively expressing K17. These positively identified target cells may be flagged to the pathologist for further review in connection with their analysis of the rescan or original WSI. FIG. 9 shows illustrative bounding boxes that may be included in a visual overlay generated by an AI engine. The visual overlay may flag target cells to a pathologist for further review or may flag target cells that the ML model determined meet a specific diagnostic threshold, such as a threshold level of K17 expression.

Figure 10:
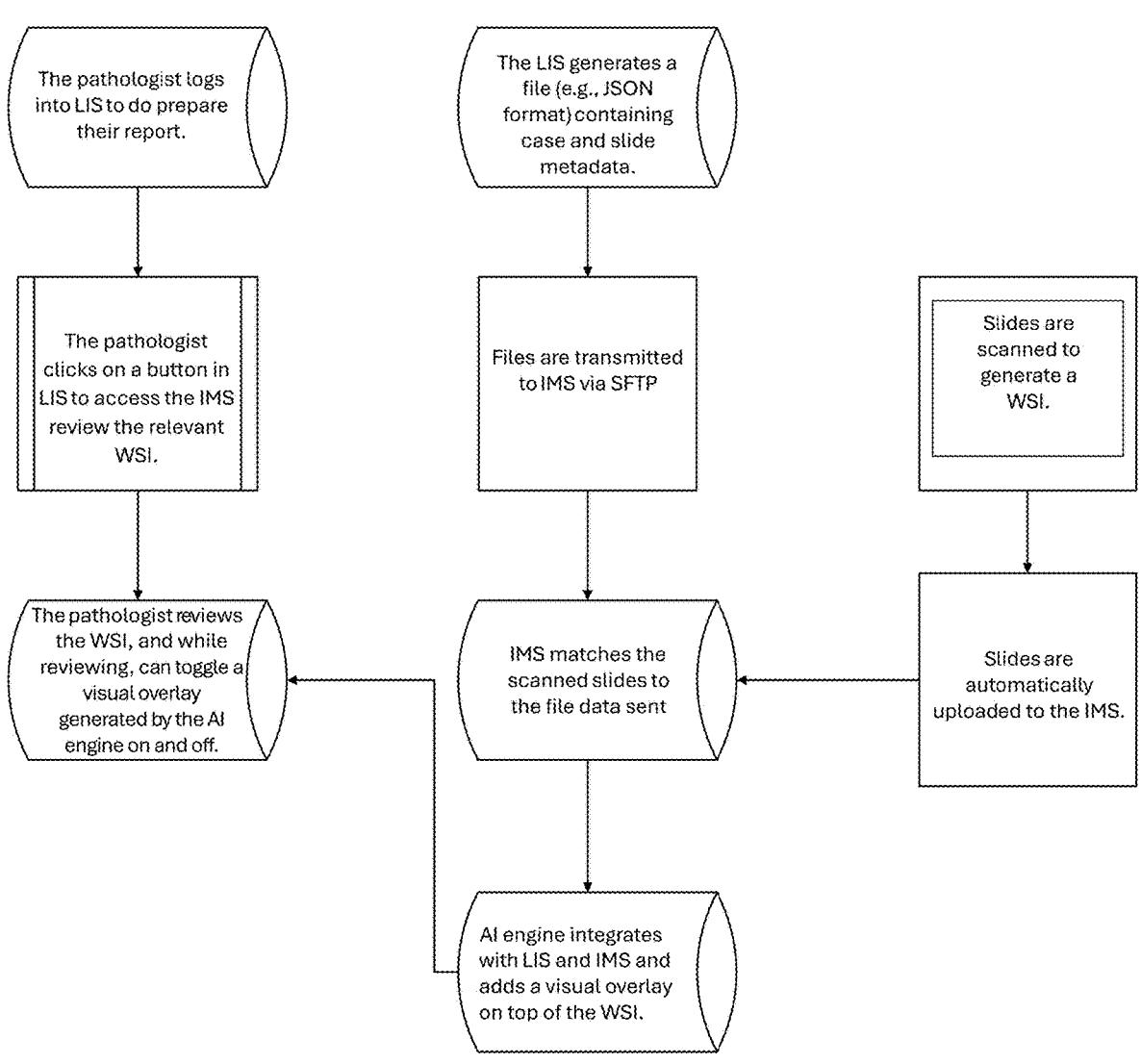
FIG. 10 shows an illustrative workflow.

FIG. 10 shows an illustrative workflow for a system that includes a Laboratory Information System (LIS), an Image Management System (IMS), and an Artificial Intelligence (AI) engine. The system and workflow shown in FIG. 10 may aid cytopathologists in reviewing whole slide images (WSIs). The workflow includes scanning a physical slide using a slide scanner. This process creates a WSI which is a high-resolution, digitized version of the glass slide. The WSI is automatically uploaded to the IMS.

The workflow includes the LIS generating a data file. The data file is transmitted to the IMS via a secure channel such as SFTP (Secure File Transfer Protocol). The creation of the data file may be automatically triggered by specific events within the workflow, such as slide printing, WSI creation or case assignment to a designated LIS user.

The data file may include case and slide metadata. The data file may store information in JSON other suitable data structures. The data file may contain important information about the case and slide being analyzed. The IMS pairs the WSI with the data file (and associated metadata) received from the LIS. This pairing links the WSI to the corresponding case and slide information.

The AI engine integrates with both the LIS and IMS. The AI engine creates a visual overlay that can be displayed with the WSI. The visual overlay may highlight areas of interest within the WSI, as identified by a ML model within the AI engine. For example, the visual overlay may highlight (e.g., using colored bounding boxes) potential abnormalities, target cells or regions of the WSI requiring closer inspection. The visual overlay may highlight diagnostic conclusions based on the ML model's analysis of the WSI.

A pathologist may log into the LIS to prepare their report regarding the WSI. The LIS may be configured such that the pathologist may click a button within the LIS to access the IMS and review the relevant WSI. While reviewing the WSI, the pathologist may toggle one or more of the visual overlays generated by the AI engine on and off. This toggling allows the pathologist to compare their own observations with the findings of the AI engine. The toggling allows the pathologist to view the raw WSI without any annotations or view the WSI with annotations generated by the ML model.

FIG. 10 shows a system and workflow that seamlessly integrates the LIS, IMS, and AI engine, streamlining analysis of a WSI. The AI engine may provide valuable insights by highlighting areas of interest, improving diagnostic accuracy and efficiency. The visual overlay generated by the AI engine allows pathologists to control the AI engine's diagnostic influence and make independent assessments.

The LIS system may identify and designate specific pathologists (e.g., users) and cases that are eligible for digital analysis. Such a mechanism may include labeling pathologists who regularly use the digital platform as "Digital Doctors." The AI engine may identify Digital Doctors based on determining that their clinical reports are associated with threshold concordance levels. The AI engine may then be configured to such the reports of such Digital Doctors as training data to further improve ML models.

For example, pathologists whose reports consistently meet or exceed a threshold level of agreement may be considered by the AI engine to have a high degree of diagnostic accuracy. The AI engine uses this concordance metric to automatically identify such pathologists (e.g., "Digital Doctors") who demonstrate a track record of reliable diagnoses, particularly within the digital pathology context. By training on the ML models using data from pathologists with proven diagnostic accuracy, the AI engine can refine its pattern recognition capabilities, learn subtle diagnostic cues that experienced pathologists utilize, improve its overall accuracy and reliability in analyzing future cases. This creates a positive feedback loop where the expertise of experienced digital pathologists directly contributes to the enhancement of the AI engine's diagnostic capabilities.

The mechanism may allow for labeling one-off cases for digital analysis. Authorized LIS system users may be linked to corresponding accounts on external platforms, such as the IMS. Data elements, such as stain IDs, may be standardized across the LIS, IMS and AI engine to ensure accurate interpretation by all systems. The LIS may regenerate and resubmit the data file in response to detection of errors or updates to the case or slide data.

The LIS may include a reporting function to enable users to monitor the status of data transfers and ensure successful processing of the data file submitted to the IMS. The systems and workflow shown in FIG. 10 may advantageously automate the integration of digital pathology into the existing LIS and IMS workflows, streamline the process of sending case information and slide data to an AI-powered analysis platform, reduce manual data entry and potential errors, and improve efficiency and accuracy in WSI review and reporting.

Figure 11:
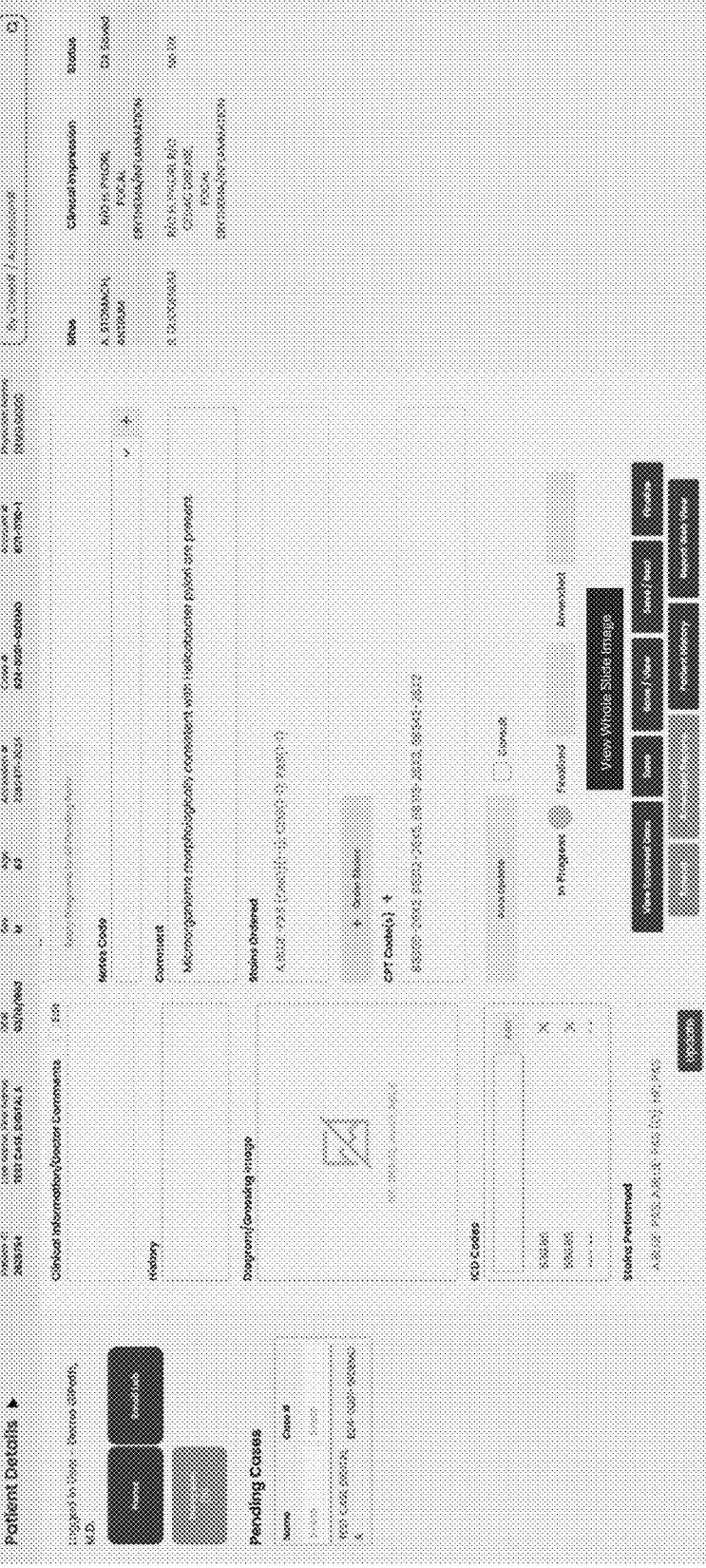
FIG. 11 shows an illustrative screenshot.

FIG. 11 shows an illustrative screenshot from an LIS showing a reporting sub-system for reviewing and delivering pathology reports. The sub-system may allow approved pathologists to review WSIs and generate and transmit pathology reports. The sub-system may allow healthcare providers or patients to access and review pathology reports.

FIG. 11 also shows that a pathologist can click the button labeled "View Whole Slide Image" and be presented with a WSI stored on an IMS. The WSI presented to the pathologist via the LIS may also include a visual overlay generated by an AI engine. The WSI may be presented with controls that allow the pathologist to toggle on or off the visual overlay.

Figure 12A:
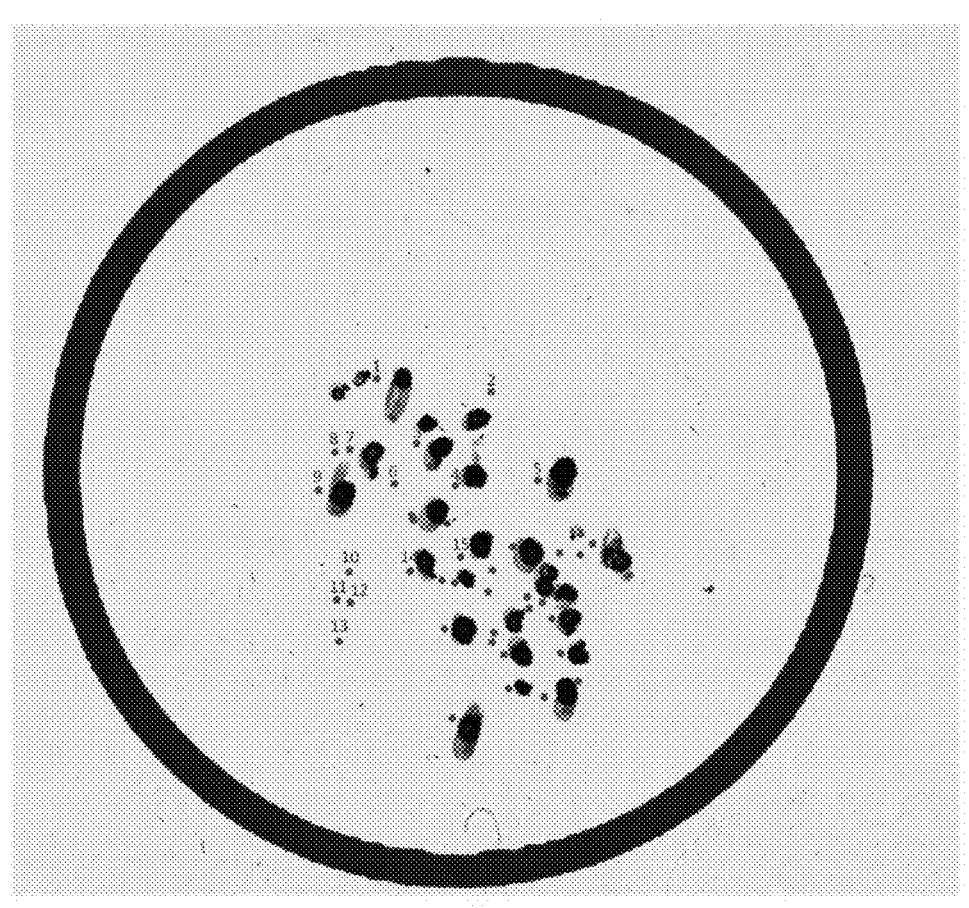
FIG. 12A shows an illustrative visual overlay.
Figure 12B:
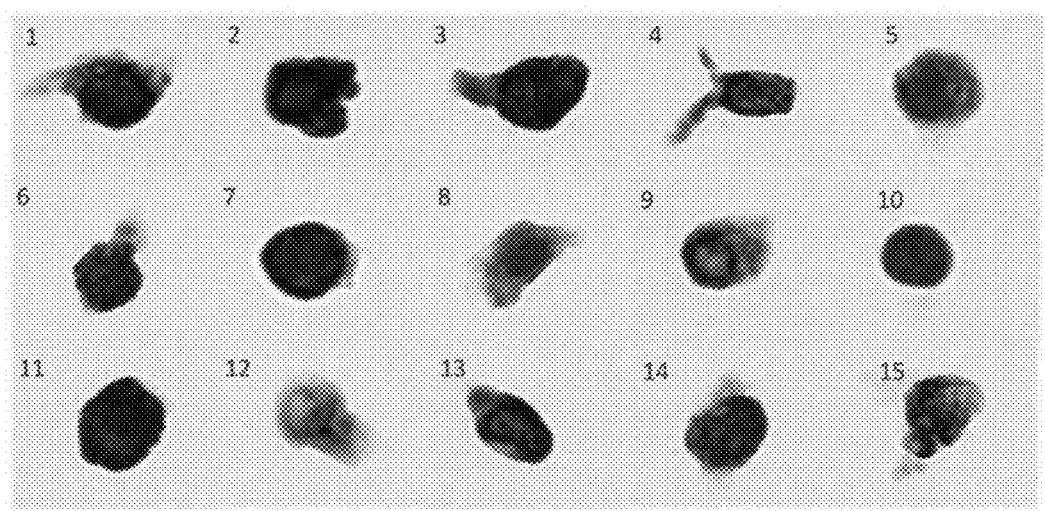
FIG. 12B shows an illustrative microscopic image associated with the visual overlay shown in FIG. 12A.

FIG. 12A shows an illustrative visual overlay that may be generated by the AI engine and presented to a LIS user. The visual overlay shown in FIG. 12A may be automatically presented to a LIS user when the user clicks to view a WSI, as described regarding FIG. 11. The illustrative visual overlay in FIG. 12A shows that the ML model has detected 15 urothelial cells in a WSI that include a threshold level of K17 expression. The visual overlay has annotated those 15 cells within the WSI using red dots and numbers. FIG. 12B shows that the LIS user can also view each of the 15 cells individually and zoomed in for closer examination and confirmation of the ML model's diagnostic determination.

FIG. 13 shows an illustrative pathology report that may be generated by an LIS after the pathologist completes review of a WSI. The LIS may be configured to generate pathology reports in connection with determining levels of K17 expression in urothelial cells. A pathology report may include a unique statement that is associated with a level of K17 expression, as determined by the number of urothelial cells in a WSI that express K17 in the WSI. Levels of K17 expression may be described in a pathology report using the following illustrative language:

1. Negative (0-4 urothelial cells): Probability of urothelial cancer is low. De-intensify cancer surveillance. Acu-UR017 results should be utilized in conjunction with urine cytology results and other known clinical risk factors to improve risk stratification in patients suspected with urothelial carcinoma.

2. LOW (5-19 Probability of cells): urothelial cancer is increased. Close monitoring, repeat testing and additional diagnostic workup should be considered. Acu-URO17 results should be utilized in conjunction with urine cytology results and other known clinical risk factors to improve risk stratification in patients suspected with urothelial carcinoma.

3. High (>20 cells): Probability of urothelial cancer is elevated. Additional testing and diagnostic workup is recommended. Acu-UR017 results should be utilized in conjunction with urine cytology results and other known clinical risk factors to further stratify overall risk of urothelial cancer.

Figure 14A:
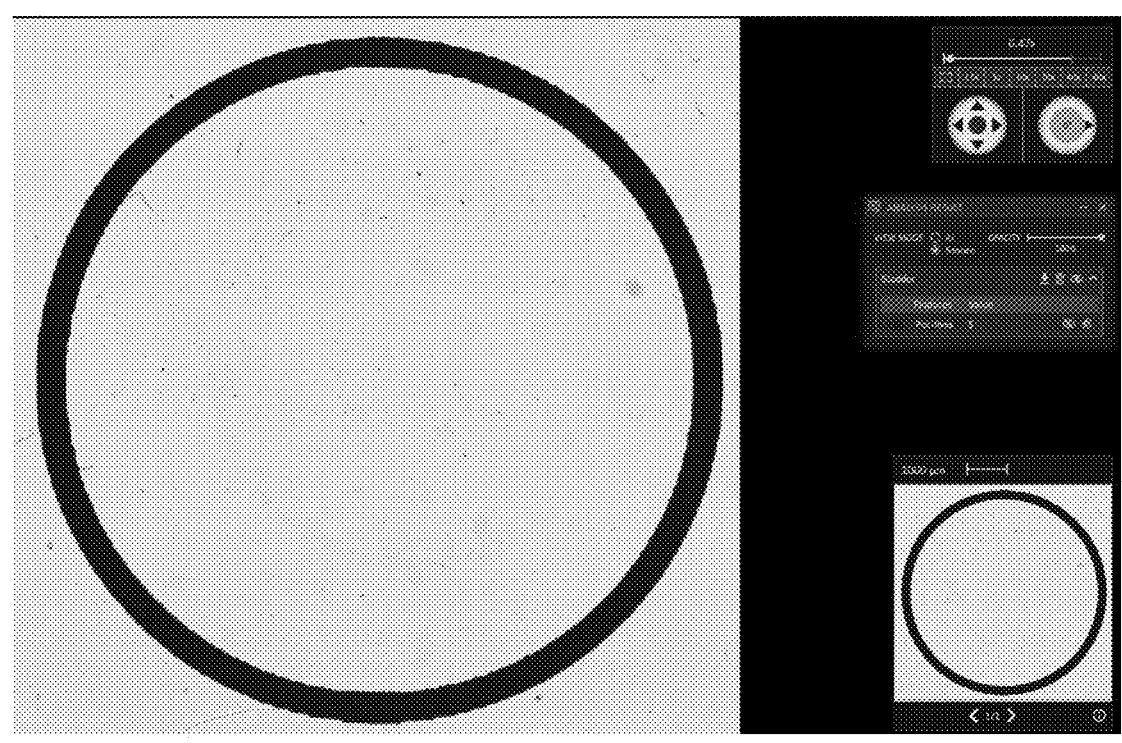
FIG. 14A shows an illustrative microscopic image.

FIG. 14A shows an illustrative "raw" WSI, presented without any annotations generated by an ML model.

Figure 14B:
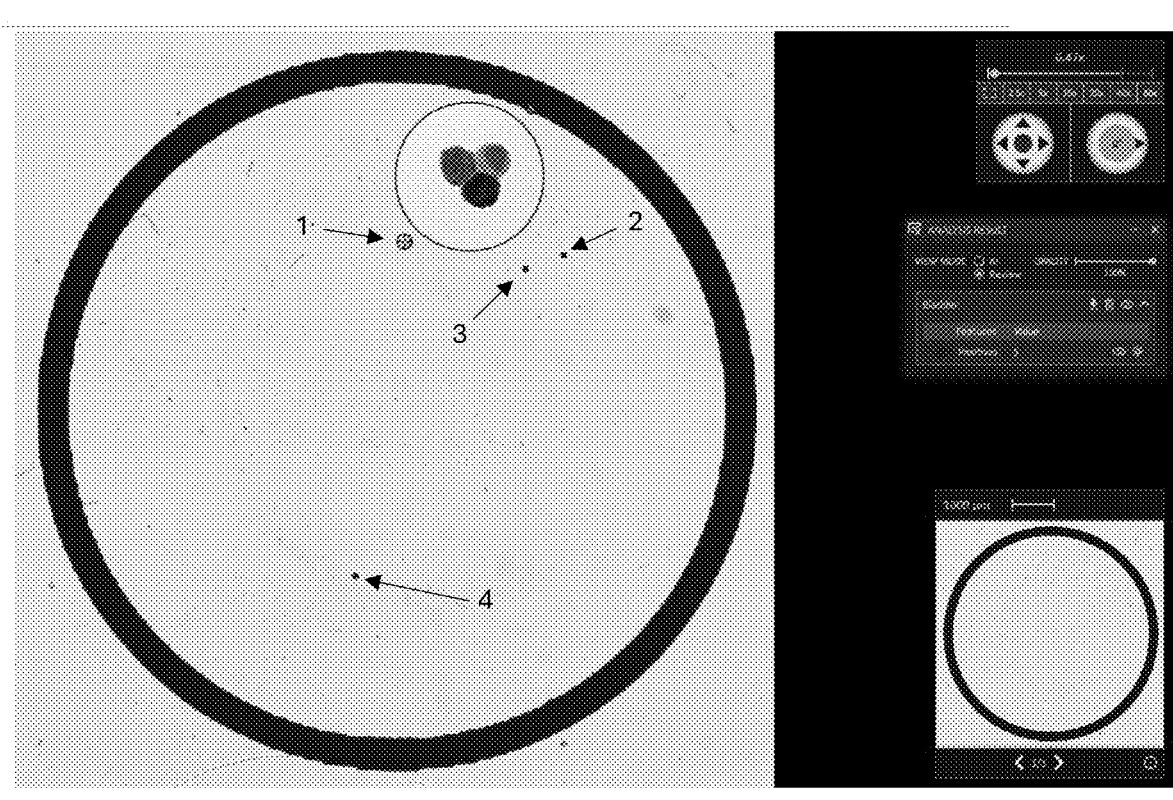
FIGS. 14B-14E show illustrative visual overlays with respect to image of FIG. 14A.

FIG. 14B shows a visual overlay generated by an AI engine that includes analysis of the WSI by an ML model. The visual overlay shown in FIG. 14B has flagged a cluster within the WSI, as indicated by the green marker (at marker #1) superimposed on the WSI. FIG. 14B also shows that clicking the green dot displays a zoomed in view of the cluster. FIG. 14B also shows that the visual overlay has identified three additional areas within the WSI (shown by markers #2, #3 and #4), and represented by three blue/purple dots within the visual overlay.

Figure 14C:
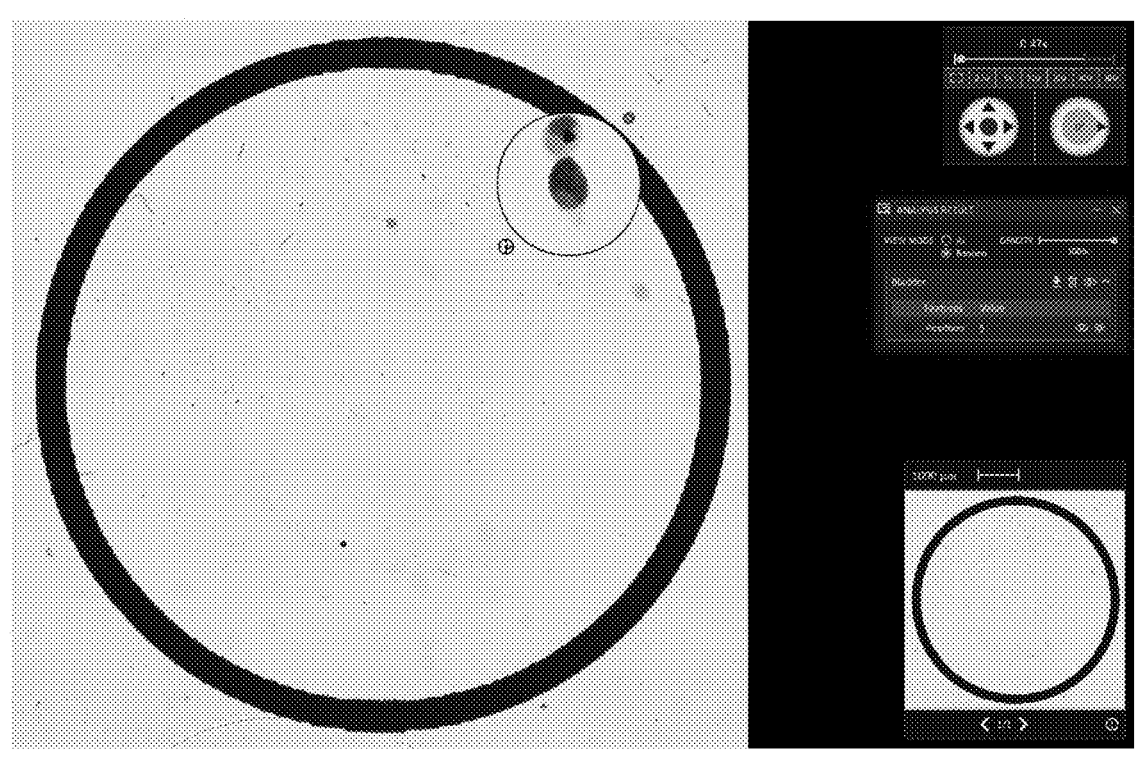

FIG. 14C shows that a first of the blue/purple dots (at marker #2) identifies a target cell within the WSI that the ML model has determined is expressing a threshold level of K17. FIG. 14C shows that the view of the target call can be zoomed in to show additional detail, such as stain intensity and cell shape.

Figure 14D:
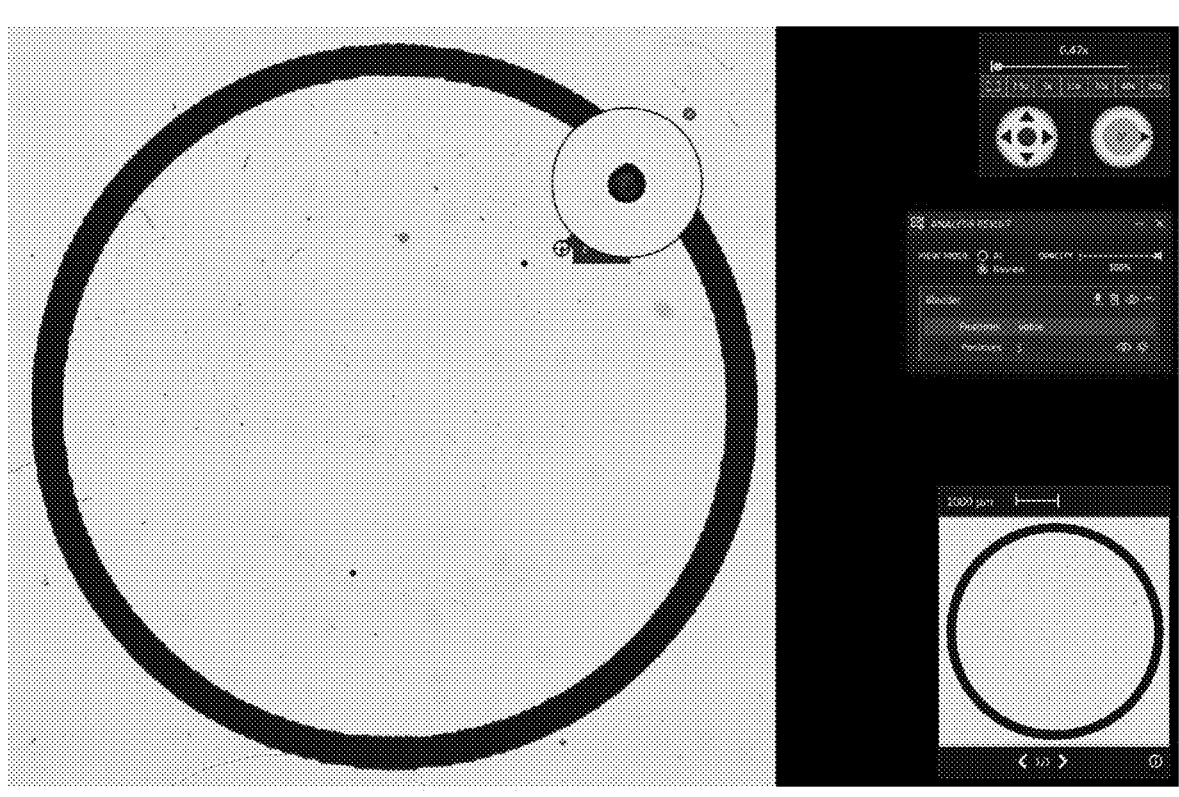

FIG. 14D shows that a second of the blue/purple dots (at marker #3) in the visual overlay represents another target cell that the ML model has identified. The visual overlay shows that the ML model has determined that the identified target cell is expressing a threshold level of K17 and has a round shape.

Figure 14E:

FIG. 14E shows that a third of the blue/purple dots (at marker #4) in the visual overlay represents yet another target cell that the ML model has identified. The visual overlay shows that the ML model has determined that the identified target cell is expressing a threshold level of K17 and has a round shape.

Thus, methods and apparatus for USE OF USE OF ARTIFICIAL INTELLIGENCE ("AL") TO DETECT THE EXPRESSION OF CYTOKERATIN 17 IN UROTHELIAL CELLS FROM PATIENTS' VOIDED URINE are provided. Persons skilled in the art will appreciate that the present invention can be practiced by other than the described embodiments, which are presented for purposes of illustration rather than of limitation, and that the present invention is limited only by the claims that follow.

What is claimed is:

1. A laboratory diagnostic system for artificial intelligence (AI) identification of urothelial cells exhibiting expression of a Cytokeratin 17 (K17) biomarker, the system comprising:

an AI engine that is configured to generate an output that identifies a target cell included in a whole slide image (WSI) that expresses the K17 biomarker; and a laboratory information system (LIS) that is configured to generate, based on the output generated by the AI engine:

a toggleable overlay that identifies the target cell included in the WSI that expresses the K17 biomarker; and a report that quantifies a level of K17 expression in the target cell;

wherein:

the target cell is one of a plurality of target cells;

the report generated by the LIS quantifies a level of K17 expressed by the plurality of target cells into low grade, medium grade, or high grade risk of carcinoma;

the low grade corresponds to less than 5 target cells in the plurality expressing the K17 biomarker;

the medium grade corresponds to 5 to 19 target cells in the plurality expressing the K17 biomarker; and the high grade corresponds to more than 19 target cells in the plurality expressing the K17 biomarker.

2. The system of claim 1 wherein:

the target cell is one of a plurality of target cells included in the WSI; and the output identifies, in the plurality of target cells, at least two of the target cells that express the K17 biomarker.

3. The system of claim 2 wherein the output of the AI engine quantifies a level of K17 expression in each of at least two of the target cells.

4. The system of claim 2 wherein the plurality of target cells comprises a cluster of at least three urothelial cells.

5. The system of claim 1, wherein the AI engine comprises a machine learning algorithm that is trained to distinguish between urothelial cells and non-cellular material in the WSI.

6. The system of claim 1 further comprising an image management system (IMS) that is configured to present the WSI with the toggleable overlay that includes the output generated by the AI engine.

7. The system of claim 6 wherein:

the LIS and IMS are configured to communicate with each other using an application programing interface (API); and via the API:

the IMS is configured to:

match the WSI to a patient record provided by the LIS; and link the output of the AI engine to the WSI; and the LIS is configured to provide access, within the patient record, to the WSI and output of the AI engine associated with WSI.

8. The system of claim 1, wherein the report is available in the LIS within 4-5 minutes after the WSI is presented to the AI engine.

9. The system of claim 1 wherein the report generated by the LIS is associated with a Cohen's kappa score that is greater than 0.5 for a level of K17 expression in the target cell as determined by a human pathologist and as determined by the output of the AI engine.

10. The system of claim 1 wherein the report generated by the LIS is associated with a Cohen's kappa score that is greater than 0.9 for a level of K17 expression in the target cell as determined by a human pathologist and as determined by the output of the AI engine.

11. The system of claim 1, further comprising:

a viewing module that is configured to present the WSI and the toggleable overlay that identifies the target cell included in the WSI that expresses the K17 biomarker.

12. The system of claim 11, wherein the target cell is a urothelial cell and the toggleable overlay flags the target cell as exhibiting urothelium duress in response to detecting a threshold level of expression of the K17 biomarker.

13. The system of claim 1 wherein:

the toggleable overlay identifies, in the plurality of target cells, at least two target cells that express a threshold level of the K17 biomarker.

14. The system of claim 1 wherein the AI engine is trained to identify the target cell as expressing the K17 biomarker if it detects that the target cell:

has a threshold level of stain intensity; and has a nucleus region that is distinct from a cytoplasmic area and edge of the target cell.

15. The system of claim 1, wherein expression of the K17 biomarker is detected based on the target cell having a threshold level of staining intensity of a target color.

16. The system of claim 1, wherein the AI engine generates the output based on a color of the target cell after applying a staining process to the target cell.

17. The system of claim 1, wherein the AI engine generates the output based on a color intensity of the target cell after applying a staining process to the target cell.

\* \* \* \* \*